(12) United States Patent
Xiao

(10) Patent No.: US 11,213,427 B2
(45) Date of Patent: Jan. 4, 2022

(54) DISPOSABLE CONTACT LENS FOR OPTICAL TREATMENT SYSTEMS

(71) Applicant: LUTRONIC VISION INC., Burlington, MA (US)

(72) Inventor: Zhen Xiao, Beijing (CN)

(73) Assignee: LUTRONIC VISION INC., Burlington, MA (US)

( * ) Notice: Subject to any disclaimer, the term of this patent is extended or adjusted under 35 U.S.C. 154(b) by 137 days.

(21) Appl. No.: 16/639,878

(22) PCT Filed: Aug. 17, 2017

(86) PCT No.: PCT/CN2017/097856
§ 371 (c)(1),
(2) Date: Feb. 18, 2020

(87) PCT Pub. No.: WO2019/033339
PCT Pub. Date: Feb. 21, 2019

(65) Prior Publication Data
US 2020/0360184 A1 Nov. 19, 2020

(51) Int. Cl.
*A61F 9/009* (2006.01)
*A61F 9/008* (2006.01)

(52) U.S. Cl.
CPC .... *A61F 9/009* (2013.01); *A61F 2009/00844* (2013.01); *A61F 2009/00863* (2013.01)

(58) Field of Classification Search
CPC ............ A61F 9/013; A61F 2009/00844; A61F 2009/00863; A61F 9/008; A61F 9/009
See application file for complete search history.

(56) References Cited

U.S. PATENT DOCUMENTS

| 5,324,281 A | 6/1994 | Muller |
| 7,115,120 B2 | 10/2006 | Lin |
| 7,836,894 B2 | 11/2010 | Brinkmann et al. |

(Continued)

FOREIGN PATENT DOCUMENTS

| CN | 101663064 A | 3/2010 |
| CN | 103764080 A | 4/2014 |

(Continued)

OTHER PUBLICATIONS

International Search Report and Written Opinion for International Application No. PCT/CN2017/097856 dated May 16, 2018, pp. 08.

*Primary Examiner* — Lynsey C Eiseman
*Assistant Examiner* — Jessica L Mullins

(57) ABSTRACT

A lens/sensor subassembly (318) may include a feedback sensor (324), a data transmission line (302), and an electrical element (328). The feedback sensor (324) may be configured to measure a phenomenon in an eye (100) of a patient during a laser-based ophthalmological therapy. The data transmission line (302) may be configured to communicate feedback data measured by the feedback sensor (324) to a laser-based ophthalmological treatment system (200). The electrical element (328) may be degradable in response to exposure to therapeutic radiation (316). The degradation of the electrical element (328) may interrupt communication of the feedback data measured by the feedback sensor (324) to the laser-based ophthalmological treatment system (200).

22 Claims, 14 Drawing Sheets

(56) References Cited

U.S. PATENT DOCUMENTS

| | | |
|---|---|---|
| 8,105,321 B2 | 1/2012 | Zemmouri et al. |
| 8,740,890 B2 | 6/2014 | Vogler |
| 10,182,941 B2 | 1/2019 | Hafezi et al. |
| 2008/0234625 A1 | 9/2008 | Dacquay et al. |
| 2009/0024117 A1* | 1/2009 | Muller ................... A61B 18/14 606/20 |
| 2015/0005750 A1* | 1/2015 | Kelleher .............. A61N 5/0625 606/3 |
| 2016/0151151 A1* | 6/2016 | Kleinman ............. A61F 2/1602 623/6.12 |
| 2016/0158058 A1 | 6/2016 | Ha |
| 2017/0216090 A1 | 8/2017 | Kim |

FOREIGN PATENT DOCUMENTS

| | | |
|---|---|---|
| WO | 01/37769 A1 | 5/2001 |
| WO | 2008/089327 A1 | 7/2008 |
| WO | 2016/018099 A1 | 2/2016 |
| WO | 2016/040534 A1 | 3/2016 |

* cited by examiner

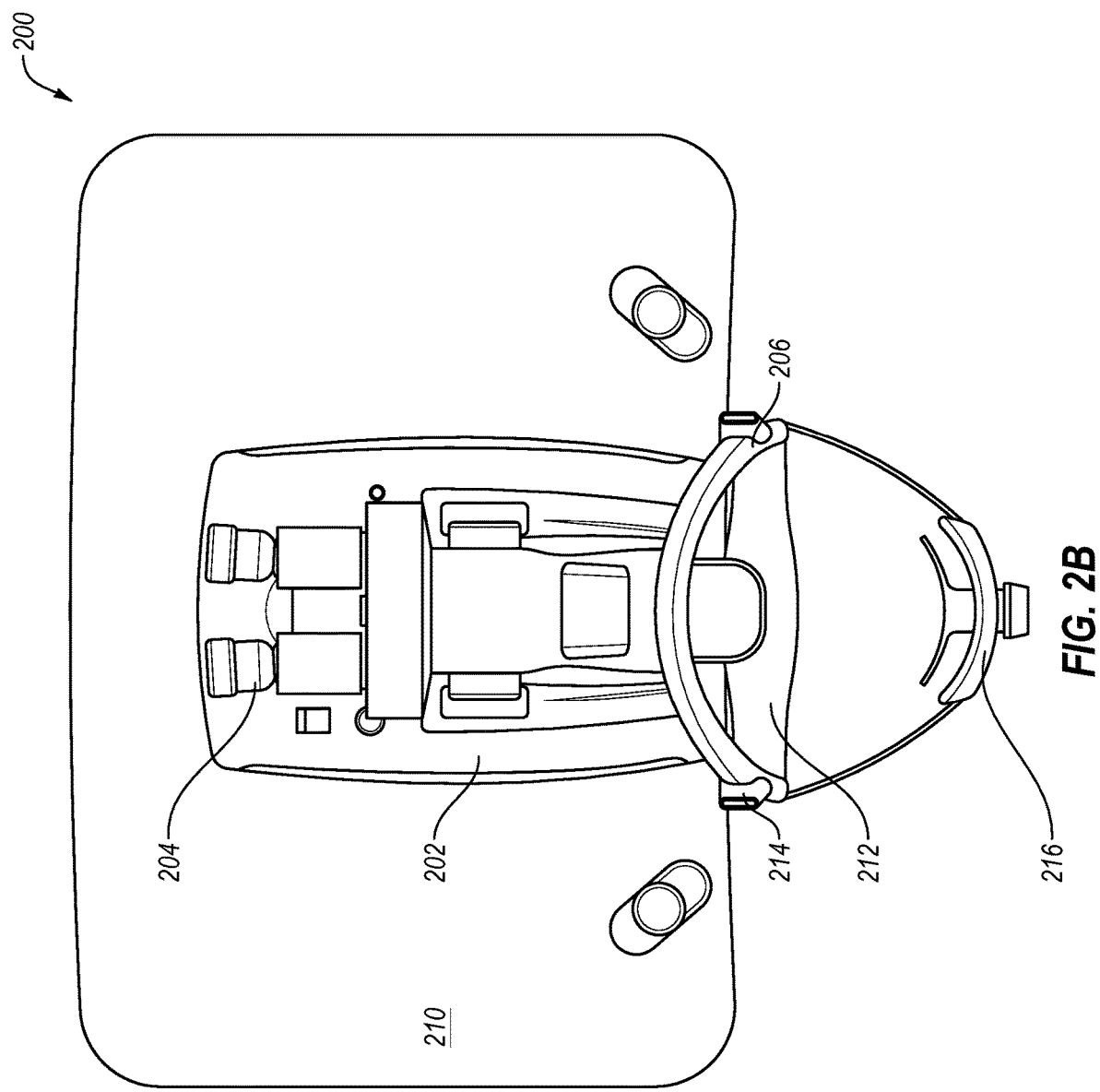

DISPOSABLE CONTACT LENS FOR OPTICAL TREATMENT SYSTEMS

CROSS-REFERENCE

This patent application is a section 371 nationalization of PCT Application No. PCT/CN2017/097856 filed Aug. 17, 2017, which PCT Application is incorporated herein by specific reference in its entirety.

BACKGROUND

Unless otherwise indicated herein, the materials described herein are not prior art to the claims in the present application and are not admitted to be prior art by inclusion in this section.

Macula disease may result in loss of vision or reduction in quality of vision of a patient. Diabetic macular edema (DME), age-related macular degeneration (AMD), and central serous chorioretinopathy (CSC) are examples of macula disease. In some circumstances, therapeutic radiation may be administered to an eye of a patient to treat the macula disease. A laser-based ophthalmological treatment system may be used in combination with a contact lens assembly to administer the therapeutic radiation. The contact lens assembly may include several components. As the contact lens assembly is used, one or more of the components may become damaged or effectiveness of one or more of the components may decrease. Additionally, the contact lens assembly may be placed in direct contact with a cornea of an eye of a patient. The direct contact may transfer contaminates such as bacteria and other biological material from the eye to the contact lens assembly. Accordingly, to improve treatment, to ensure effective treatment, and/or to minimize cross-contamination between patients, the contact lens assembly may be disposable and replaced between patients or following a particular amount of use.

However, it may be difficult to ascertain when components lose their effectiveness. Moreover, multiple sterilizations of the contact lens may cause uneven heating inside the contact lens and may scratch a surface of the contact lens, which may lead to increase the lens scattering. Thus, contact lens assemblies with ineffective components may be used during treatments, which may result in an unsafe condition for patients. Additionally, replacement of the contact lens assembly may increase costs associated with administration of the treatments, which may incentivize reuse to avoid such costs.

SUMMARY

Techniques described herein generally relate to therapeutic radiation treatment systems and methods.

In an example embodiment, a contact lens assembly may include an assembly housing, an input lens, and a lens/sensor subassembly. The assembly housing may define a first opening and a second opening. The second opening may be opposite the first opening. The input lens may be positioned in the first opening. The lens/sensor subassembly may be positioned in the second opening. The lens/sensor subassembly may include a contact lens, a feedback sensor, a data transmission line, an electrical element, and a beam splitter. The contact lens may be arranged on an optical path that may be aligned with a pupil of an eye of a patient. The feedback sensor may be configured to measure a phenomenon in the eye during a laser-based ophthalmological therapy. The data transmission line may be configured to communicate feedback data measured by the feedback sensor to a laser-based ophthalmological treatment system (hereinafter, "treatment system"). The electrical element may electrically couple the feedback sensor to the data transmission line. The beam splitter may be partially positioned on the optical path. The beam splitter may be configured to direct a portion of a therapeutic radiation emitted through the contact lens towards the electrical element. The electrical element may be degradable by exposure to the portion of the therapeutic radiation. The degradation of the electrical element may interrupt an electrical coupling between the feedback sensor and the data transmission line.

In another example embodiment, a lens/sensor subassembly may include a feedback sensor, a data transmission line, and an electrical element. The feedback sensor may be configured to measure a phenomenon in an eye of a patient during a laser-based ophthalmological therapy. The data transmission line may be configured to communicate feedback data measured by the feedback sensor to a treatment system. The electrical element may be degradable in response to exposure to therapeutic radiation. The degradation of the electrical element may interrupt communication of the feedback data measured by the feedback sensor to the treatment system.

In yet another example embodiment, a treatment system may include a therapeutic radiation source, a dosimetry board, a contact lens assembly, a head fixation assembly, and a microscope. The dosimetry board may be coupled to the therapeutic radiation source. The contact lens assembly may be optically coupled to the therapeutic radiation source.

The contact lens assembly may include a feedback sensor, a data transmission line, and an electrical element. The feedback sensor may be configured to measure a phenomenon in the eye during the therapeutic treatment. The data transmission line may be configured to communicate feedback data measured by the feedback sensor to the dosimetry board. The electrical element may be degradable in response to exposure to therapeutic radiation from the therapeutic radiation source. Degradation of the electrical element may interrupt communication of the feedback data measured by the feedback sensor to the dosimetry board. The head fixation assembly may be configured to position and retain a head of a patient with an eye of a patient optically aligned to the contact lens assembly to receive therethrough therapeutic radiation emitted by the therapeutic radiation source. The microscope may be optically coupled to the contact lens assembly to allow an operator of the treatment system to view the eye of the patient during therapeutic treatment of the eye of the patient with the treatment system.

In another example embodiment, a method of laser-based ophthalmological treatment may include directing therapeutic radiation towards an eye of a patient. The method may include diverting a portion of the therapeutic radiation towards an electrical element. The method may include detecting an open circuit condition of the electrical element after the electrical element is degraded by the portion of therapeutic radiation. The method may include stopping treatment of the eye in response to detection of the open circuit condition.

In another example embodiment, a method of preventing reuse of a contact lens assembly in a treatment system may include directing therapeutic radiation towards an eye through a contact lens assembly. The method may include diverting a portion of the therapeutic radiation towards an electrical element associated with the contact lens assembly such that the electrical element degrades. The method may include detecting an open circuit condition of the electrical element after the electrical element is degraded by the portion of the therapeutic radiation. The method may include stopping use of the contact lens assembly when the open circuit condition is detected.

In some embodiments, a contact lens assembly can include: an assembly housing that defines a first opening and a second opening that is opposite the first opening; an input lens positioned in the first opening; a lens/sensor subassembly positioned in the second opening. In some aspects, the lens/sensor subassembly includes: a contact lens that is arranged in an optical path; a feedback sensor; a data transmission line configured to communicate feedback data measured by the feedback sensor to a laser-based ophthalmological treatment system; an electrical element that electrically couples the feedback sensor to the data transmission line; and a beam splitter that is partially positioned in the optical path. In some aspects, the beam splitter is configured to direct at least a portion of a therapeutic radiation towards the electrical element. In some aspects, the electrical element is configured to degrade]responsive to exposure to the portion of the therapeutic radiation.

In some embodiments, the feedback sensor comprises at least one of an acoustic sensor, an ultrasonic sensor, or a ring shaped acoustic sensor positioned about at least a portion of the contact lens in the optical path.

In some embodiments, the electrical element comprises one or more of a wire mesh, an alloy metal that melts responsive to the at least a portion of the therapeutic radiation, or an electrical element that interrupts an electrical coupling between the feedback sensor and the data transmission line.

In some embodiments, the electrical element comprises one or more of: an electrical element that is at least partially constructed of a conductive polymer; an electrical element that is at least substantially transparent; a wire mesh; an electrical element with an alloy metal that melts responsive to exposure to therapeutic radiation; or an electrical element that interrupts an electrical coupling between the feedback sensor and the data transmission line.

In some embodiments, a lens/sensor subassembly can include: a feedback sensor; a data transmission line configured to communicate feedback data measured by the feedback sensor to a laser-based ophthalmological treatment system; and an electrical element that is electrically coupled between the feedback sensor and the data transmission line. In some aspects, the electrical element is configured to degrade in response to exposure to therapeutic radiation.

In some embodiments, the feedback sensor surrounds at least a portion of the contact lens such that feedback sensor is positioned outside of an optical path of the contact lens. In some aspects, a printed circuit board (PCB) that is electrically coupled to the feedback sensor and wherein the PCB substantially surrounds at least a portion of the contact lens.

In some embodiments, a laser-based ophthalmological treatment system comprising: a therapeutic radiation source; a dosimetry board coupled to the therapeutic radiation source; the lens/sensor subassembly of one of the embodiments optically coupled to the therapeutic radiation source; a head fixation assembly configured to position and retain a head of a patient with an eye of a patient optically aligned to the lens/sensor subassembly to receive therapeutic radiation emitted by the therapeutic radiation source; and a microscope optically coupled to the lens/sensor subassembly. In some aspects, a patient contact lens assembly retainer can be configured to selectively retain the lens/sensor subassembly in the laser-based ophthalmological treatment system, wherein the lens/sensor subassembly is disposable and removable. In some aspects, the technology can include affixing a head of the patient relative to a head fixation assembly that is configured to position and retain the head of the patient.

In some embodiments, the methods can include preventing reuse of a contact lens assembly in a laser-based ophthalmological treatment system by: directing the therapeutic radiation towards an eye through a contact lens assembly; diverting the portion of the therapeutic radiation towards an electrical element associated with the contact lens assembly such that the electrical element degrades; and stopping use of the contact lens assembly when the open circuit condition is detected. In some aspects, prior to detection of the open circuit condition, the method can include receiving feedback data measured by a feedback sensor and following detection of the open circuit condition, ceasing reception of the feedback data.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information, as well as other features of this disclosure, will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings:

FIG. 2B illustrates another view of the system of FIG. 2A;

DETAILED DESCRIPTION

Figure 1A:
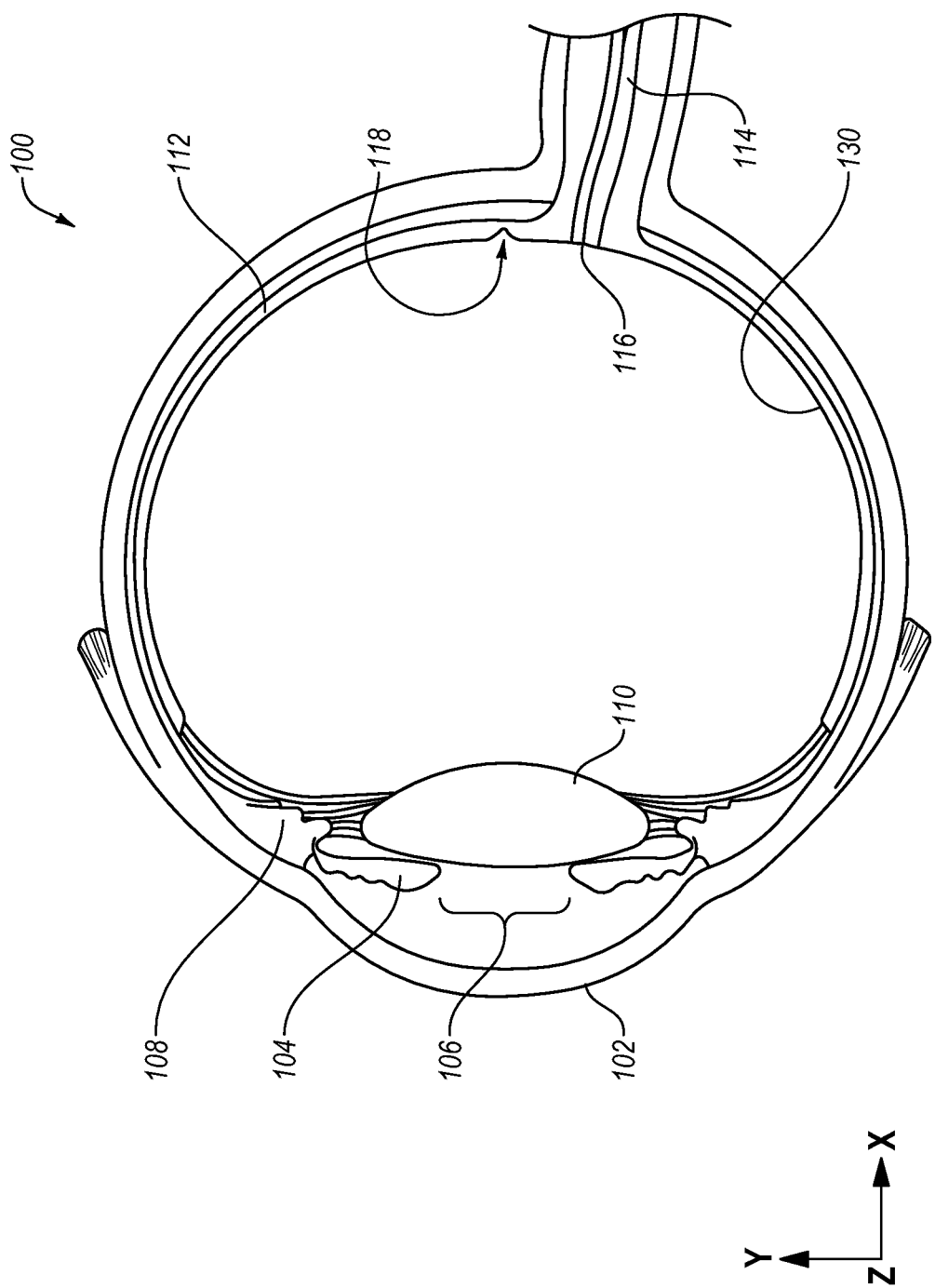
FIG. 1A is a cross-sectional view of an example human eye (hereinafter "eye")

This disclosure is generally drawn to methods, apparatus, systems, devices, and computer program products related to therapeutic radiation dosimetry.

In this detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

Macula disease such as diabetic macular edema (DME), age-related macular degeneration (AMD), and central serous chorioretinopathy (CSC) may result in vision impairment or vision loss. Treatment of the macula disease may involve administration of a therapeutic radiation by a laser-based ophthalmological surgical system (system). The therapeutic radiation may be emitted through a contact lens assembly, through a pupil of an eye of a patient, and to a fundus of the eye. A surface of a contact lens of the contact lens assembly may be placed in direct physical contact with a cornea of the eye. The contact lens assembly may include a feedback sensor that is configured to measure phenomena of the eye during administration of the therapeutic radiation. The phenomena may be measured in real time or in substantially real time. Feedback data representative of the phenomena may be communicated to the system from the contact lens assembly. Based on the feedback data, one or more operating parameters of the therapeutic radiation may be set, altered, or otherwise determined. For instance, in response to the feedback data including acoustic data indicating creation and/or dispersion of bubbles within the eye, the system may cease administration of the therapeutic radiation. Some additional details of the detection of the feedback data in an example embodiment are provided in WO 2016018099, which is incorporated herein by reference in its entirety.

Functionality of the feedback sensor or another component of the contact lens assembly may decrease through use. Additionally, the direct physical contact with the cornea may cause contamination of the contact lens. Accordingly, some embodiments described in the current disclosure relate to systems and methods to prevent reuse of the contact lens assembly or some component(s) thereof. For example, in some embodiments, the contact lens assembly includes a lens/sensor subassembly. The lens/sensor subassembly includes a feedback sensor, a data transmission line, and an electrical element. The feedback sensor may be configured to measure a phenomenon in an eye of a patient during a laser-based ophthalmological therapy. The data transmission line may be configured to communicate feedback data measured by the feedback sensor to a treatment system.

In an initial state, the electrical element may be configured to communicate electrical signals with an initial resistance. The electrical element may be degradable in response to exposure to therapeutic radiation. Following degradation, resistance and/or inductance in the electrical element may change. For instance, following the degradation, the electrical element may read as an open electrical connection (infinite resistance or near infinite resistance) or may change from a first resistance (e.g., 1 milliohm) to a second resistance (e.g., 15 milliohm). The system with which the contact lens assembly is implemented may respond to the change in the resistance of the electrical element. For instance, the system may be rendered inoperable based on the change in resistance of the electrical element. For example, in some embodiments, the electrical element may electrically couple the feedback sensor to the transmission line. The electrical element may be introduced into an optical path of the therapeutic radiation or may be positioned such that a portion of the therapeutic radiation is directed towards the electrical element. Exposure to the therapeutic radiation may degrade the electrical element, which may interrupt the feedback data communicated to the system. Without the feedback data, the system may cease emission of the therapeutic radiation. To continue the therapeutic radiation, the contact lens assembly or the lens/sensor subassembly may be replaced.

FIG. 1A is a cross-sectional view of an example human eye (hereinafter "eye") 100. The eye 100 may include a cornea 102, an iris 104, a pupil 106, a ciliary body 108, a lens 110, a retina 112, a fundus 130, and an optic nerve 114. The retina 112 generally includes a light-sensitive layer of tissue upon which optics of the eye 100 project an image of the visual world external to the eye 100. Through a series of chemical and electrical events, nerve impulses may be triggered in response to light striking the retina 112. The nerve impulses may be processed in vision centers of the brain such that the visual world may be perceived by a person.

The fundus 130 of the eye 100 includes an interior surface of the eye 100 opposite the lens 110. The fundus 130 may include a portion of the retina 112. The retina 112 includes an optic disc 116, sometimes referred to as the "blind spot." The retina 112 may also include a macula 118. The macula 118 may be separated from the optic disc 116 on the retina 112. The eye 100 may rotate in a socket to view an object. Rotation of the eye 100 may orient the pupil 106 and the retina 112 to receive light from the object. The pupil 106 allows the light to enter the eye 100. When the eye 100 moves, the pupil 106 and the retina 112 may move in the y-direction and/or the z-direction of an arbitrarily defined Cartesian coordinate system of FIG. 1A. Additionally, in response to the light, a diameter of the pupil 106 may change.

The ciliary body 108 may be attached to the lens 110 via zonula fibers 132. The ciliary body 108 may change a shape of the lens 110 as the eye 100 focuses on the object. The shape of the lens 110 may dictate how the light strikes the retina 112.

Figure 1B:
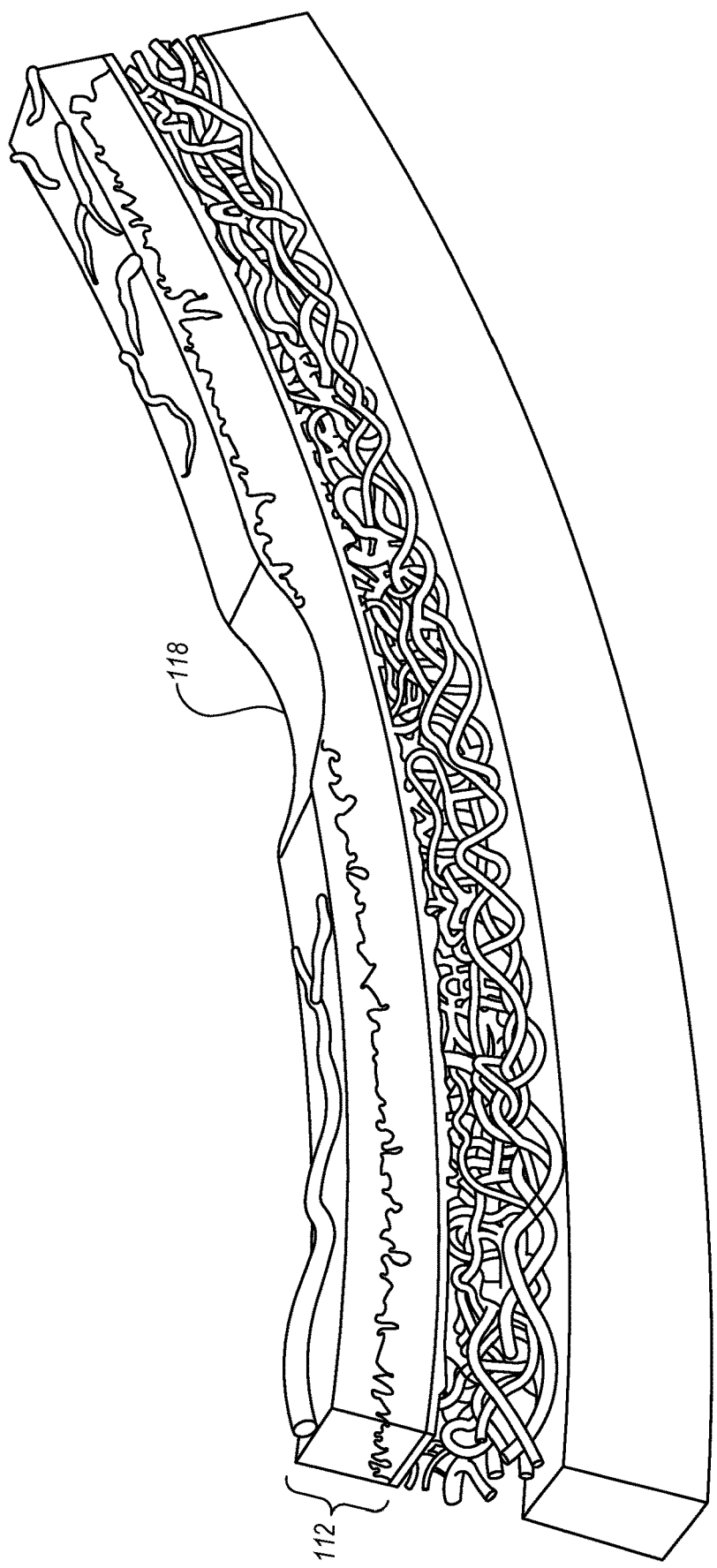
FIG. 1B is a cross-sectional perspective view of a portion of a retina and a macula of FIG. 1B.

FIG. 1B is a cross-sectional perspective view of a portion of the retina 112 and the macula 118 of FIG. 1A.

Figure 1C:
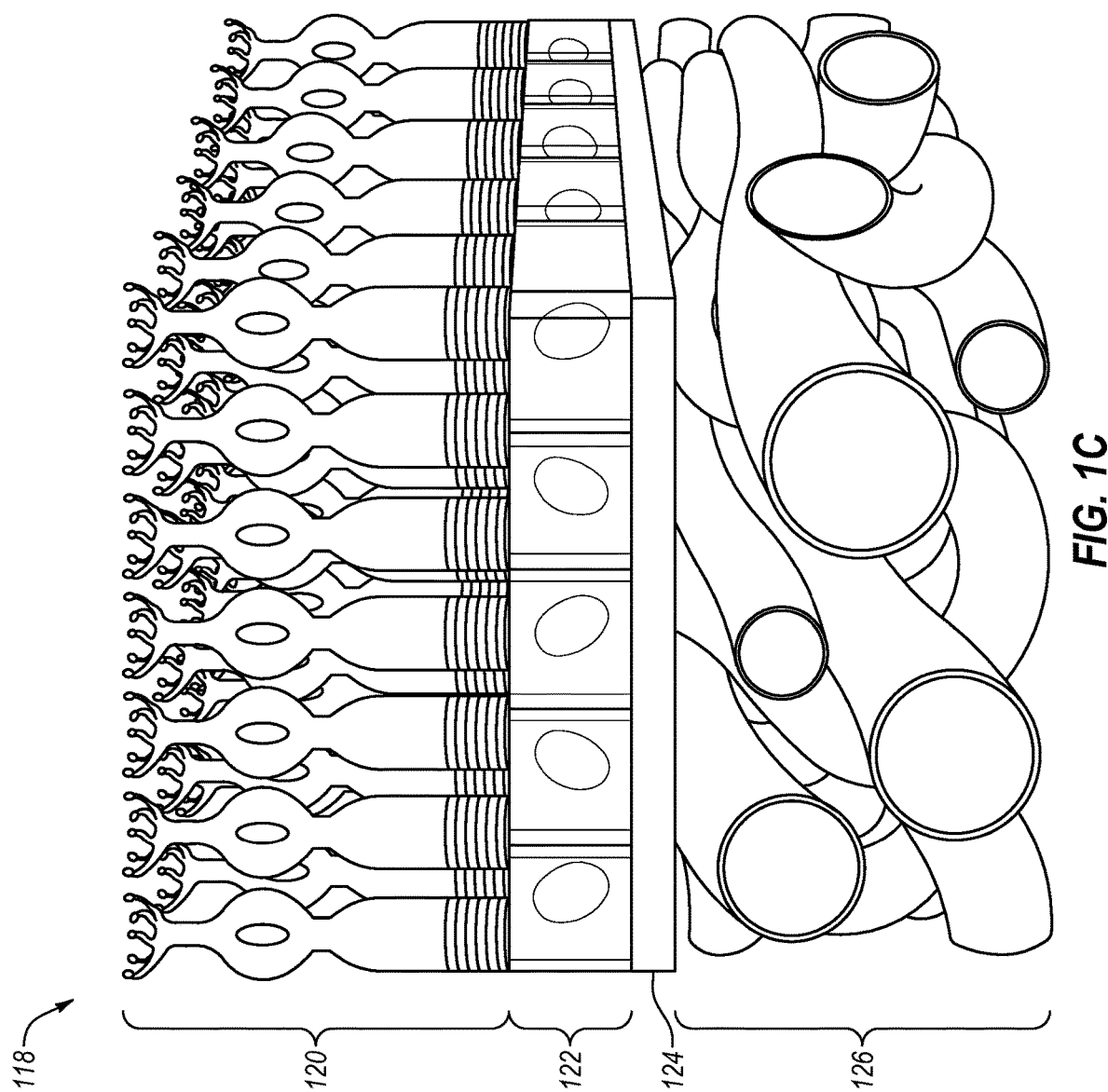
FIG. 1C is a cross-sectional perspective view of a portion of the macula of FIG. 1B.

FIG. 1C is a cross-sectional perspective view of a portion of the macula 118 of FIG. 1B. FIG. 1C depicts various layers that may make up the macula 118, including photoreceptors 120, retinal pigment epithelial (RPE) cells 122, Bruch's membrane 124, and the choroid 126. The macula 118 may have a relatively high concentration of photoreceptors 120 compared to the rest of the retina 112 and without blood vessels, for central and/or high-resolution vision. The RPE cells 122 may nourish the photoreceptors 120 by supplying nutrients from the choroid 126 and transporting extracellular material out through the Bruch's membrane 124.

Various conditions may adversely affect vision in the eye 100. For instance, with reference to FIGS. 1A-1C, AMD may involve degradation of the RPE cells 122 in the macula 118. In dry AMD, degraded RPE cells 122 may fail to transport extracellular material which may then begin to build up ("Drusen") in between the Bruch's membrane 124 and the RPE cells 122. The Drusen may interfere with the supply of nutrients to the photoreceptors 120, which can lead to vision loss. In wet AMD, new blood vessels (neovascularization) may grow from the choroid 126 and penetrate the Bruch's membrane 124 and the RPE cells 122 to supply nutrients to the photoreceptors 120. The new blood vessels may be weak and prone to bleeding and leakage, which may result in blood and protein leakages, which in turn may damage the photoreceptors 120 and fuel rapid vision loss.

Another condition that may adversely affect vision in the eye 100 may be DME. In more detail, persons with diabetes may experience a slowing of metabolism over time, which may reduce the ability of retinal vessels to deliver enough nutrients, which in turn may induce neovascularization. Fluid leakage from the neovascularization may cause the retina 112 to swell, causing vision loss.

Another condition that may adversely affect vision in the eye 100 may be CSC. In CSC, leakage of fluid accumulates under the central macula 118, resulting in blurred or distorted vision, which may progressively decline with each recurrence.

Some embodiments described herein include a laser-based ophthalmological surgical system that includes a therapeutic radiation source configured to emit therapeutic radiation to treat AMD, DME, CSC, and/or other conditions of the eye 100.

Figure 2A:
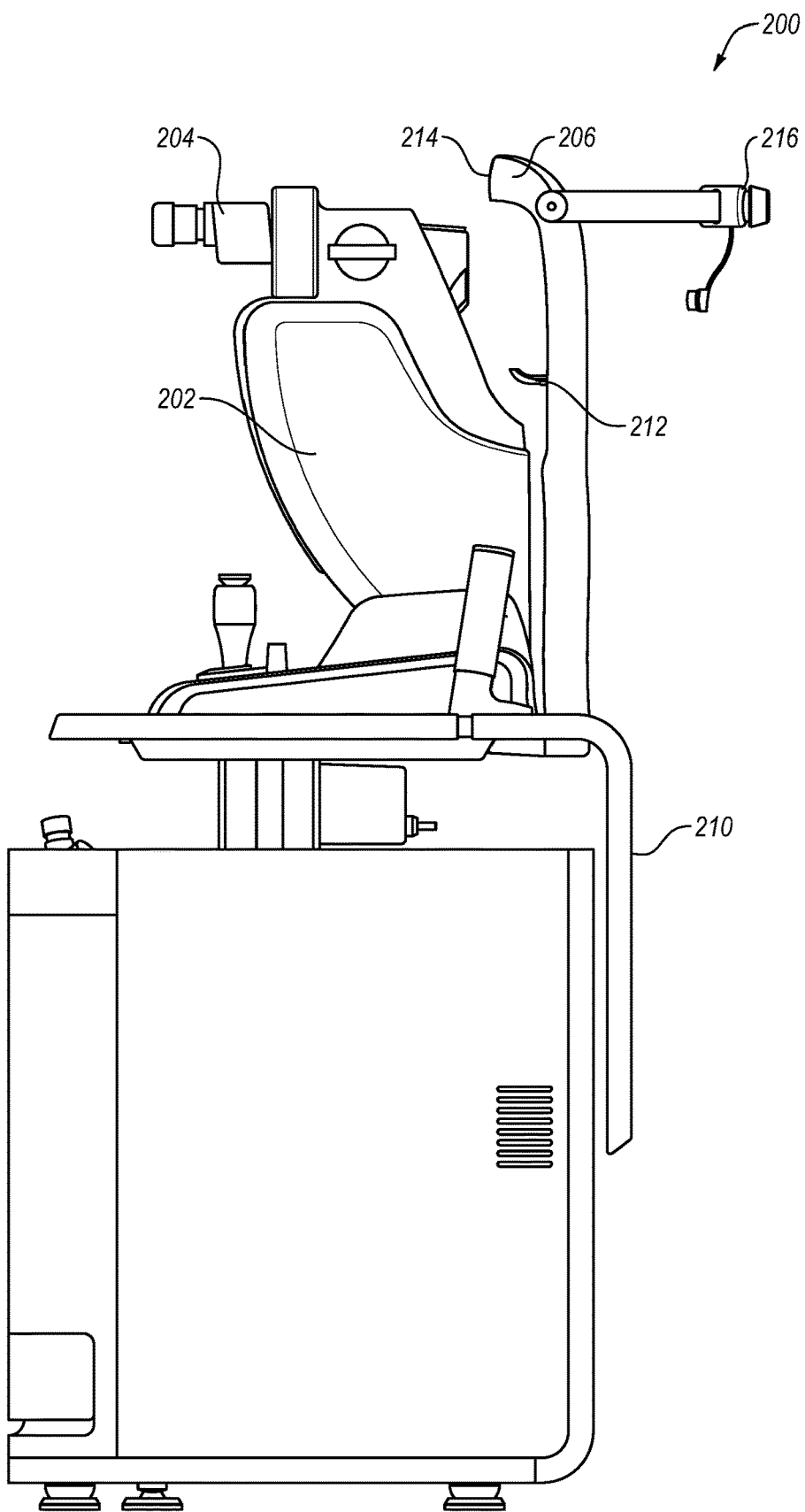
FIG. 2A illustrates an example laser-based ophthalmological surgical system (hereinafter "system")
Figure 2C:
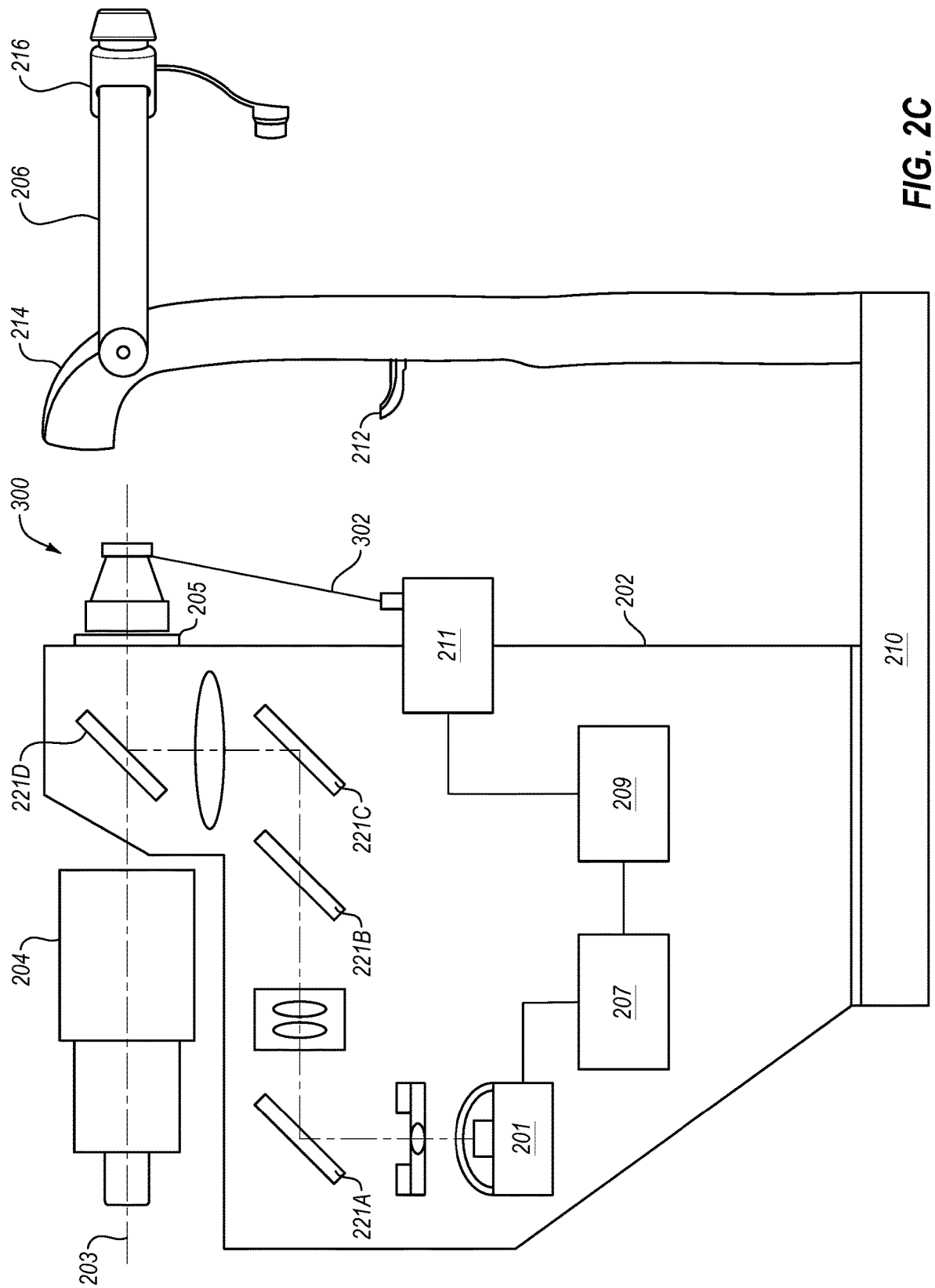
FIG. 2C illustrates another view of the system of FIG. 2A.

FIGS. 2A-2C illustrate an example laser-based ophthalmological treatment system 200 (hereinafter, "treatment system 200"), arranged in accordance with at least one embodiment described herein. FIG. 2A is an exterior side view of the treatment system 200. FIG. 2B is an exterior top view of the treatment system 200. FIG. 2C is a section view of the treatment system 200. The treatment system 200 may be configured to administer laser-based treatment of an ocular disease (e.g., AMD, DME, CSC, and/or other conditions of the eye). For example, in some embodiments, the treatment system 200 may be configured to emit therapeutic radiation into an eye of a patient such as the eye 100 described with reference to FIG. 1A. The therapeutic radiation may selectively damage retinal pigment epithelial (RPE) cells or other cells in a diseased portion of the eye. New cells may regenerate to replace the damaged cells, which may reduce or eliminate the effect of the ocular disease.

The treatment system 200 may include a device housing 202, a microscope 204, and a head fixation assembly 206. As shown in FIGS. 2A and 2B, the device housing 202, the microscope 204, and the head fixation assembly 206 may be visible. The device housing 202 may be positioned apart from the head fixation assembly 206 and may be fixed relative to the head fixation assembly 206. For instance, in some embodiments, the device housing 202 may be secured to a base 210 at a first location. The head fixation assembly 206 may also be secured to the base 210 at a second location. The head fixation assembly 206 may accordingly be fixed relative to the device housing 202. In some embodiments, the head fixation assembly 206 may be secured directly to the device housing 202 or otherwise fixed relative to the device housing 202.

The device housing 202 may surround or partially surround components of the treatment system 200. For instance, the device housing 202 may partially surround the microscope 204. A first portion of the microscope 204 into which a healthcare provider looks may be external to the device housing 202. A second portion of the microscope 204 (e.g., lenses, focus elements, etc.) may be positioned within the device housing 202. The microscope 204 may be positioned in an optical path to allow an operator to view the eye of the patient.

The head fixation assembly 206 may be configured to position and to retain a head of the patient relative to the device housing 202. Accordingly, once fixed within the head fixation assembly 206, the head of the patient may be positioned and retained relative to the device housing 202 and/or the microscope 204.

In some embodiments, the head fixation assembly 206 may include a jaw portion 212, a forehead rest 214, and a fixing band 216. A jaw of the patient may be placed in the jaw portion 212 and a forehead of the patient may be placed against the forehead rest 214. The fixing band 216 may be placed and tightened around the head to fix the head in the head fixation assembly 206.

Prior to emission of the therapeutic radiation, a diseased portion of the eye may be diagnosed. Diagnosis of the diseased portion may be based on a fundus image of the eye. To acquire the fundus image, the head of the patient may be fixed in the head fixation assembly 206. For instance, the patient may place their jaw against the jaw portion 212 and may place their forehead against the forehead rest 214. The fixing band 216 may be placed around the head and tightened to fix the head relative to the head fixation assembly 206. With the head of the patient fixed in the head fixation assembly 206, a portion of the fundus of the eye may be aligned with the optical path of the treatment system 200. Following the alignment, the fundus image may be acquired. The fundus image may include a portion of the fundus (e.g., the fundus 130 of FIG. 1A) that may include a diseased portion such as a fundus lesion. Based on the fundus image, the ocular disease may be diagnosed.

In response to the diagnosis of the diseased portion, the patient may return one or more times for administration of the therapeutic radiation. To administer the therapeutic radiation by the treatment system 200, the head of the patient may be re-fixed in the head fixation assembly 206 such that the head may be fixed relative to the device housing 202 and components therein. The portion of the fundus may be re-aligned with the optical path. The therapeutic radiation may be emitted through a pupil of the eye to treat the diseased portion of the fundus. There may be multiple events in which the therapeutic radiation is administered.

FIG. 2C depicts an example arrangement of components that may be positioned within the device housing 202. In FIG. 2C, the treatment system 200 is depicted with a contact lens assembly 300. The contact lens assembly 300 may include one or more components that are configured to prevent its reuse or limit its use. For example, the contact lens assembly 300 may include a component that degrades in response to exposure to the therapeutic radiation. Degradation of the component may prevent or interrupt communication of the feedback data to the treatment system 200. Prevention or interruption of communication of the feedback data may result in an unsafe operation of the treatment system 200.

Additionally or alternatively, degradation of the component may be otherwise sensed by the treatment system 200. For example, the treatment system 200 may sense an open circuit, a circuit with a particular resistance, or a circuit with a particular characteristic change. In response, the treatment system 200 may cease emission of the therapeutic radiation. Accordingly, the contact lens assembly 300 may be replaced with another contact lens assembly 300 in which the component has not been degraded.

The treatment system 200 may include a therapeutic radiation source 201, a controller board 207, a dosimetry board 209, and an amplifier board 211. The therapeutic radiation source 201 may be configured to emit or transmit the therapeutic radiation. The therapeutic radiation may be emitted at least partially along an optical path, which is represented in FIG. 2C by a dashed line 203.

The therapeutic radiation may be emitted through the contact lens assembly 300 and to the eye of the patient. The therapeutic radiation may be in a form of a short-pulse laser. The therapeutic radiation may be configured to specifically target a layer of the retina of the eye such as the RPE cells (e.g., the RPE cells 122 of the retina 112 of FIGS. 1A-1C).

In an example embodiment, the therapeutic radiation is administered to the targeted RPE cells 122 in pulses with a pulse duration of between half a microsecond to several microseconds, such as 1.7 microseconds. The administration of the therapeutic radiation may be periodic in some embodiments, with a pulse frequency in a range from 50 hertz (Hz) to 200 Hz (corresponding to a period in a range of 0.02 seconds to 0.005 seconds), such as about 100 Hz (corresponding to a period of 0.01 seconds). For instance, multiple therapeutic radiation pulses, each with a pulse duration of 1.7 microseconds, may be sequentially administered with a pulse frequency of 100 Hz. The administration of pulses may be terminated in response to feedback indicating a maximum exposure to the therapeutic radiation. In some embodiments, a pulse type and/or pulse control of the therapeutic radiation may be in a range of about 500 nanometers (nm) to about 600 nm or about 527 nm. Additionally or alternatively, the therapeutic radiation may be emitted in multiple pulses. For instance, the therapeutic radiation may be emitted in sets of between about 9 and about 20 pulses or about 15 pulses. In some other embodiments, the therapeutic radiation may include operating characteristics similar to those described in U.S. Pat. Nos. 7,115,120 and 7,836,894, which are incorporated herein by reference in their entireties.

In some embodiments, the therapeutic radiation may be generally more effective at treating conditions of the eye at higher exposure levels. However, at a particular level of exposure (e.g., power) to the therapeutic radiation, therapeutic radiation may cause excessive damage to the eye that may result in vision loss. To avoid or reduce the likelihood of vision loss due to excessive exposure to the therapeutic radiation while permitting exposure up to a sufficiently high level to be effective, some embodiments described herein may start administration of the therapeutic radiation at a relatively low exposure that ramps up with each successive pulse until real-time feedback indicates a threshold exposure has been reached. In an example, the first pulse of therapeutic radiation may be at about 50% of a relatively high energy level, such as a maximum energy level. More generally, the first pulse may be at a relatively low energy level, and each successively administered pulse of therapeutic radiation may be increased compared to the preceding pulse. The amount of increase from pulse to pulse may be fixed or variable. For instance, in an example embodiment, the amount of increase from pulse to pulse may be fixed at 5% of the relatively high energy level.

The therapeutic radiation source 201 may be positioned outside of the optical path 203. The therapeutic radiation may be redirected or transmitted by one or more optical elements 221A, 221B, 221C, and 221D to the optical path 203. In other embodiments, the therapeutic radiation source 201 may be positioned on the optical path 203.

The therapeutic radiation source 201 may be coupled to the dosimetry board 209. The dosimetry board 209 may be electrically coupled between the amplifier board 211 and the controller board 207. The amplifier board 211 may be electrically coupled to the contact lens assembly 300 or a feedback sensor included therein.

According to some embodiments, the treatment system 200 may use real-time feedback from the contact lens assembly 300 to determine a time during which the therapeutic radiation is administered to the eye of the patient. For example, during the administration of the therapeutic radiation, the contact lens assembly 300 may communicate feedback data to the amplifier board 211. The amplifier board 211 may communicate the feedback data or some representation thereof to the dosimetry board 209. The dosimetry board 209 may communicate the feedback data or some derivation thereof to the controller board 207. Based on the feedback data or some derivation thereof, an operating condition or characteristic of the therapeutic radiation source 201 may be altered.

For example, in some embodiments, the contact lens assembly 300 or a feedback sensor included therein may be configured to detect RPE damage and stop therapeutic radiation automatically based on the feedback prior to excessively damaging the targeted RPE cells. In these and other embodiments, the real-time feedback may measure exposure of the targeted RPE cells to the therapeutic radiation by measuring the formation and/or bursting of microbubbles that form on melanosomes of the targeted RPE cells in response to exposure to the therapeutic radiation. In an example embodiment, the formation and/or bursting of the microbubbles may be measured with optical feedback and/or acoustic feedback. In particular, the targeted RPE cells may reflect and/or emit optical and/or acoustic signals that may vary depending on the presence, absence, and/or characteristics (e.g., size, velocity) of the microbubbles. Excessive exposure to the therapeutic radiation after microbubble formation and RPE damage could damage other retinal structures, which may lead to formation of scotoma on the retina.

In some embodiments, the treatment system 200 may include an input device 213. The input device 213 may receive input from a healthcare provider. The input may include a command signal, for instance, that may determine an operational state of the therapeutic radiation source 201 or another component of the treatment system 200.

The contact lens assembly 300 may be used to focus the therapeutic radiation emitted by the therapeutic radiation source 201. The contact lens assembly 300 may be disposable or may include one or more disposable portions (e.g., lens/sensor subassembly 318 described elsewhere in this disclosure). For instance, after use of the contact lens assembly 300 with a particular patient, the contact lens assembly 300 or one or more portions thereof may be discarded.

For instance, multiple sterilization of the contact lens assembly 300 may cause uneven heating inside the contact lens assembly 300 and may scratch a surface of the contact lens assembly 300, which may lead to increase the lens scattering. Thus, the contact lens assembly 300 with ineffective components may be used during treatments, which may result in an unsafe condition for patients.

The contact lens assembly 300 may be positioned between the device housing 202 and the head fixation assembly 206. The contact lens assembly 300 may be placed directly on the eye of a patient. In some embodiments, the contact lens assembly 300 may be held in a hand of a healthcare provider during diagnosis and/or treatment of the eye of a patient. For instance, the healthcare provider may be positioned such that the healthcare provider may view and/or operate the microscope 204. With the head of the patient fixed in the head fixation assembly 206, the healthcare provider may hold the contact lens assembly 300 against the cornea of the eye of the patient. When the contact lens assembly 300 is placed on the cornea of the eye, the contact lens assembly 300 may be oriented along the optical path 203.

In some embodiments, the system may include a patient contact lens assembly retainer 205. The patient contact lens assembly retainer 205 may be coupled to the device housing 202. The patient contact lens assembly retainer 205 may be configured to selectively retain the contact lens assembly 300 relative to the device housing 202. For instance, instead of or in addition to the contact lens assembly 300 being held by the healthcare provider, the contact lens assembly 300 may be retained in the patient contact lens assembly retainer 205.

The contact lens assembly 300 may include a data transmission line 302. The data transmission line 302 may electrically couple the amplifier board 211 with the contact lens assembly 300 or a component thereof. Data such as feedback data measured at the contact lens assembly 300 may be communicated to the amplifier board 211 via the data transmission line 302.

Figure 3:
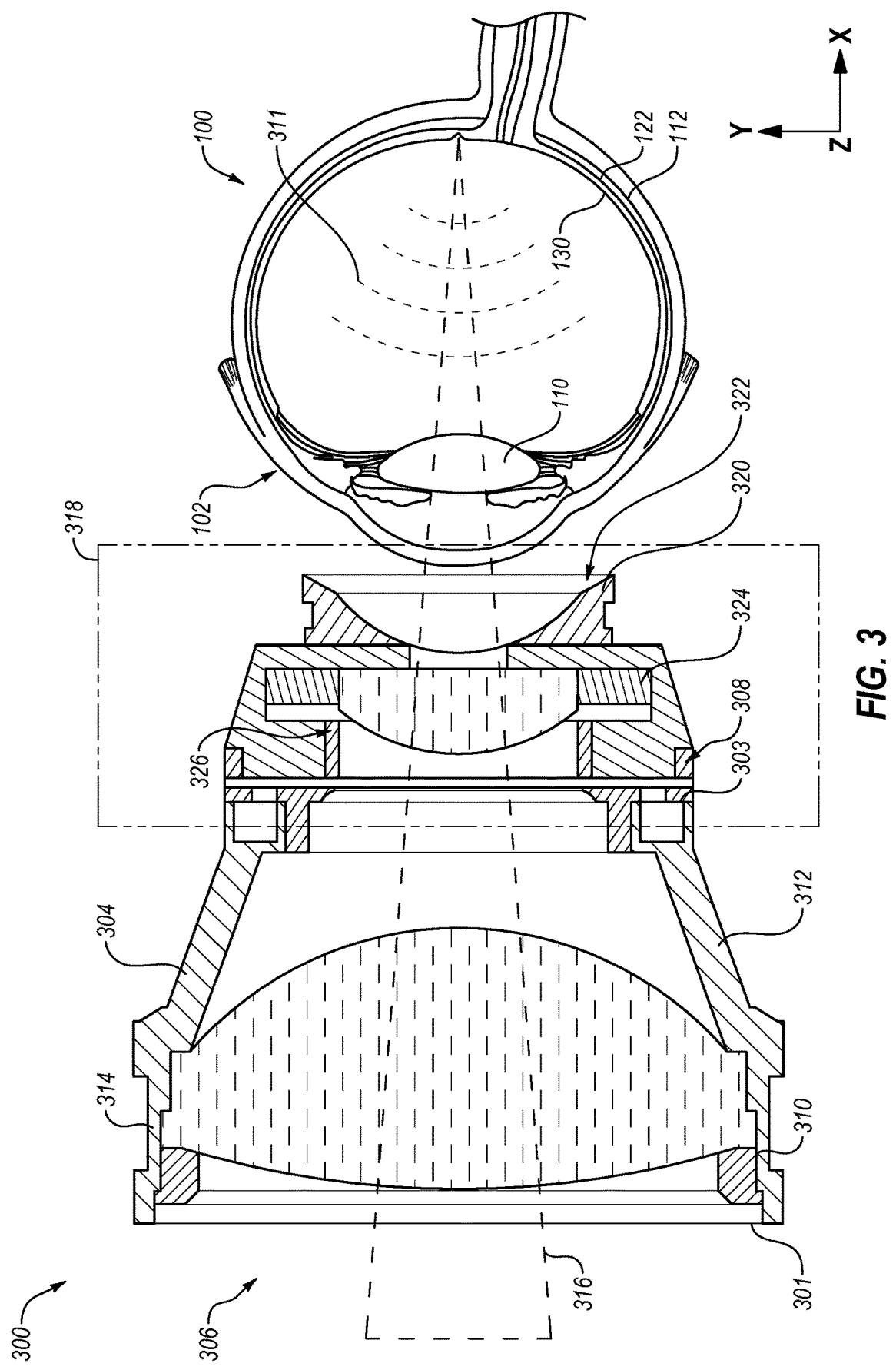
FIG. 3 is a block diagram of an example contact lens assembly that may be implemented in the system of FIGS. 2A-2C.

FIG. 3 illustrates an example embodiment of the contact lens assembly 300 that may be implemented in the treatment system 200 of FIGS. 2A-2C. In FIG. 3, the contact lens assembly 300 is depicted with the eye 100 of FIG. 1A. In FIG. 3, a sectional view of the contact lens assembly 300 is depicted.

The contact lens assembly 300 may include an assembly housing 304. The assembly housing 304 may define a first opening 306 at a first end 301 and a second opening 308 at a second end 303. The second opening 308 may be positioned opposite the first opening 306. The assembly housing 304 may include a generally cylindrical portion 310 that is connected to a generally conical portion 312. The first opening 306 may be defined by the generally cylindrical portion 310. The second opening 308 may be defined by the generally conical portion 312.

The contact lens assembly 300 may include an input lens 314. The input lens 314 may be positioned close to or at the first end 301. For example, the input lens 314 may be positioned in the generally cylindrical portion 310. Additionally or alternatively, the input lens 314 may be positioned at least partially in the first opening 306. The input lens 314 may be configured to receive therapeutic radiation from a treatment system such as the treatment system 200 of FIGS. 2A-2C. For example, with combined reference to FIGS. 2C and 3, the contact lens assembly 300 may be positioned along the optical path 203. In particular, the contact lens assembly 300 may be positioned such that the input lens 314 is oriented along the optical path 203. Therapeutic radiation may be emitted by the therapeutic radiation source 201 and enter the contact lens assembly 300 via the input lens 314. In FIG. 3, the therapeutic radiation 316 emitted by the system is represented by a conical shape.

The contact lens assembly 300 may include a lens/sensor subassembly 318. The lens/sensor subassembly 318 may be positioned at least partially in the second opening 308 of the assembly housing 304. Between the lens/sensor subassembly 318 and the input lens 314, the contact lens assembly 300 may include an empty or substantially empty volume through which the therapeutic radiation 316 is transmitted.

The lens/sensor subassembly 318 may include a contact lens 320. The contact lens 320 may be positioned opposite the input lens 314. Accordingly, the therapeutic radiation 316 may enter the contact lens assembly 300 via the input lens 314, pass through the empty space between the contact lens 320 and the input lens 314, and then pass through the contact lens 320 before entering the eye 100. As described below, in some embodiments, only a portion of the therapeutic radiation 316 may pass through the contact lens 320.

The contact lens 320 may include a contact surface 322 and an interior surface 326. The contact surface 322 may be configured for direct physical contact with the eye 100. For example, the contact surface 322 may be curved to conform to the cornea 102 of the eye 100. The interior surface 326 may be positioned in the space between the input lens 314 and the contact lens 320.

As the therapeutic radiation 316 passes through the contact lens assembly 300, the therapeutic radiation 316 may be focused. For example, the input lens 314 and the contact lens 320 may focus the therapeutic radiation 316. Additionally, the lens 110 may focus the therapeutic radiation 316. Accordingly, the therapeutic radiation 316 may be focused onto a portion of the fundus 130.

The lens/sensor subassembly 318 may include a feedback sensor 324. The feedback sensor 324 may be configured to measure a phenomenon in the eye 100. For example, as the therapeutic radiation 316 is emitted to the portion of the fundus 130, the feedback sensor 324 may be configured to measure the phenomenon in real time.

As described above, the feedback sensor 324 may be configured to detect damage to the RPE cells 122 in the retina 112 of the eye 100. In particular, the feedback sensor 324 may include an acoustic sensor such as an ultrasonic sensor. As the RPE cells 122 are exposed to the therapeutic radiation 316, microbubbles may form and/or burst. The formation and/or bursting of the microbubbles may produces an audio phenomenon 311 in the eye 100. Feedback data representative of the audio phenomenon 311 may be communicated to a treatment system such as the treatment system 200 of FIGS. 2A-2C from the feedback sensor 324. For instance, with reference to FIGS. 2C and 3, the feedback data may be communicated via the data transmission line 302.

In response to the feedback data that indicates formation and/or bursting of the microbubbles, the treatment system may cease emission of the therapeutic radiation 316. Some additional details of the lens/sensor subassembly 318 are provided with reference to FIGS. 4A and 4B.

The contact lens assembly 300 may include one or more components that are configured to prevent its reuse or limit its use. In some embodiments, the lens/sensor subassembly 318 may be configured to prevent reuse or limit use of the contact lens assembly 300 or portions thereof through rendering inoperable one or more functions of the contact lens assembly 300. For example, the lens/sensor subassembly 318 may include a component that degrades in response to exposure to the therapeutic radiation 316. Degradation of the component may prevent or interrupt communication of the feedback data to the treatment system. Prevention or interruption of communication of the feedback data may result in an unsafe operation of the system. For instance, a healthcare provider may not be alerted to the formation and/or bursting of the microbubbles.

Additionally or alternatively, degradation of the component may be otherwise sensed by the treatment system. For example, the treatment system may sense an open circuit, a circuit with a particular resistance, or a circuit with a particular characteristic change. In response, the system may cease emission of the therapeutic radiation. In these and other embodiments, a condition imposed by the degradation of the component may be maintained. For example, the degradation may result in changes to resistance and/or induction of the component. Accordingly, the contact lens assembly 300 and/or the lens/sensor subassembly 318 may be replaced with another in which the component has not been degraded.

Figure 4A:
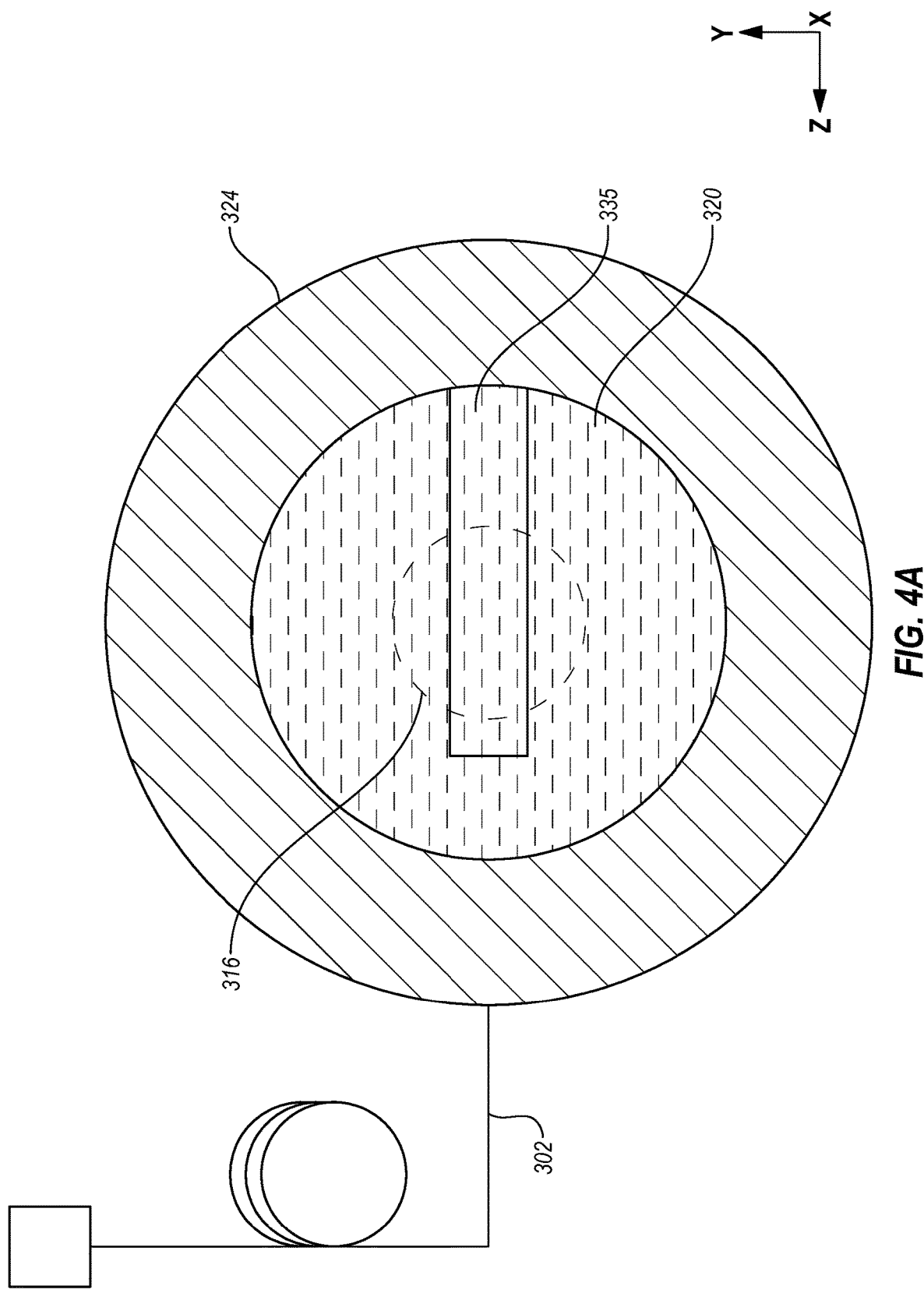
FIG. 4A is an example lens/sensor subassembly that may be implemented in the contact lens assembly of FIG. 3.
Figure 4B:
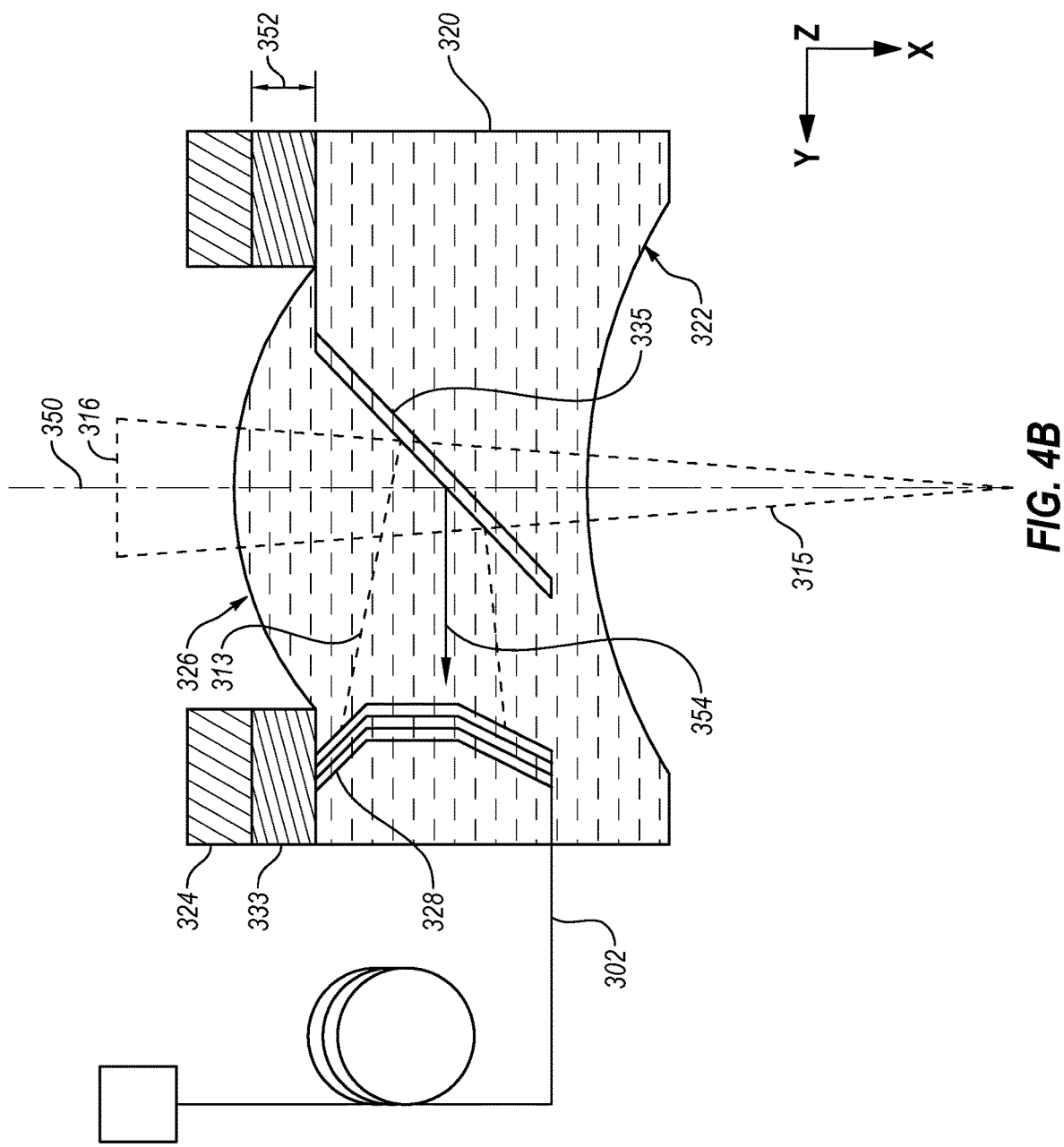
FIG. 4B is another view of the lens/sensor subassembly of FIG. 4A.

FIGS. 4A and 4B depict block diagrams of an example embodiment of the lens/sensor subassembly 318 of FIG. 3. FIG. 4A is an end view of the lens/sensor subassembly 318. FIG. 4B is a side sectional view of the lens/sensor subassembly 318. The lens/sensor subassembly 318 may be oriented according to an arbitrarily defined coordinate system, which is consistent in FIGS. 3, 4A, and 4B.

With reference to FIGS. 4A and 4B, the lens/sensor subassembly 400 may include the contact lens 320, the feedback sensor 324, a printed circuit board (PCB) 333 (FIG. 4B), the data transmission line 302 (FIG. 4B), an electrical element 328 (FIG. 4B), and a beam splitter 335 (FIG. 4B).

The PCB 333 may be electrically connected to the feedback sensor 324. For instance, the PCB 333 may include one or more electrical contacts that correspond to and/or contact one or more electrical contacts on the feedback sensor 324. The feedback data measured by the feedback sensor 324 may be communicated to the PCB 333 via the electrical contacts. In the embodiment of FIGS. 4A and 4B, the PCB 333 and the feedback sensor 324 may be ring-shaped. For instance, in the YX plane the PCB 333 and the feedback sensor 324 may be rings. In some embodiments, the PCB 333 and/or the feedback sensor 324 may have another shape such as a rectangle, a portion of a ring (e.g., an arc), or another suitable shape. The PCB 333 and the feedback sensor 324 may have substantially similar shapes (e.g., the ring-shape) or may have different shapes. For instance, the feedback sensor 324 may have a ring-shape and the PCB 333 may include an arc that extends around a portion of the feedback sensor 324. Additionally, in some embodiments, the PCB 333 may be omitted. The PCB 333 and/or the feedback sensor 324 may surround at least a portion of the contact lens 320. For instance, a portion of the interior surface 326 may extend into a volume defined by the ring-shape of the PCB 333 and/or the feedback sensor 324. The PCB 333 may have a thickness 352. The thickness 352 may be oriented in the x-direction of FIG. 4B. The thickness 352 may be determined such that the PCB 333 fits within a contact lens assembly such as the contact lens assembly 300 of FIG. 3. For instance, in some embodiments, the thickness may be between about 0.3 millimeters (mm) and about 1.0 mm or may be about 0.6 mm.

The data transmission line 302 may be configured to communicate the feedback data to the system. In particular, the data transmission line 302 may be configured to communicate feedback data measured by the feedback sensor 324 to a treatment system. The data transmission line 302 may external to the lens/sensor subassembly 318. Alternatively, at least some portion of the data transmission line 302 may be internal to the contact lens 320. The electrical element 328 electrically couples the feedback sensor 324 to the data transmission line 302. In the lens/sensor subassembly 318, the electrical element 328 may be indirectly electrically coupled to the feedback sensor 324 via the PCB 333. In some embodiments, e.g., embodiments in which the PCB 333 is omitted, the electrical element 328 may be directly electrically coupled to the feedback sensor 324.

The electrical element 328 may be degradable by exposure to the therapeutic radiation 316. For instance, the electrical element 328 may include a wire mesh. The wire mesh may be integrated into the contact lens 320. The wire mesh may be constructed of an alloy metal. The alloy metal may melts in response to exposure to the therapeutic radiation 316 or to a particular amount of the therapeutic radiation. For instance, the therapeutic radiation may heat the electrical element 328 such that discontinuities develop between the PCB 333 and the data transmission line 302. The discontinuities may increase an electrical resistance between the PCB 333 and the data transmission line 302. In some embodiments, the discontinuities may have infinite or near infinite resistance.

In an example embodiment, wires in the wire mesh may include a wire space that is comparable with the laser spot size. An example laser spot size may be about 200 micrometers (μm). Additionally, in these and other embodiments, a wire diameter of the wire mesh may be about 50-60 μm. In some therapeutic treatments, one shot may include about 15 pulses. Also, each patient may be subject to a maximum of about 1000 shots. Accordingly, the wire mesh may be configured to withstand about 15,000 pulses. A treatment energy may be about 350 micro Joules. Accordingly, a fuse threshold may be about 0.7 micro Joules assuming in embodiments in which about 90% energy passes through to the wire mesh. In some embodiments, a metal thickness of the wire mesh may be about 0.1 μm to about 1 μm. Additionally, in some embodiments, the wire mesh may be constructed of Aluminum or of Aluminum with Copper.

In embodiments in which the maximum is about 1000 pulses or another suitable number of pulses, a counter may be included. The counter may track the number of pulses such that a healthcare professional may be aware of the number of pulses since the last replacement.

In another example, the electrical element 328 may be constructed of a conductive polymer. For instance, the electrical element 328 may be constructed of a Polythiophenes, a Polypyrroles, a Polyaniline, or some combination thereof. The electrical element 328 constructed of the conductive polymer may be degraded in response to the therapeutic radiation 316 which may increase an electrical resistance of the electrical element 328. Degradation of the electrical element 328 interrupts an electrical coupling between the feedback sensor 324 and the data transmission line 302. Accordingly, following degradation of the electrical element 328, a treatment system electrically coupled to the data transmission line 302 may receive indication of an open circuit or an increased resistance. In response, the treatment system may cease emission of the therapeutic radiation 316 or otherwise alert a healthcare provider who may be administering the therapeutic radiation 316.

As discussed with reference to FIG. 3, the contact lens 320 may be arranged on an optical path 350. The optical path 350 may correspond to the optical path 203 of FIG. 2C when a contact lens assembly (e.g., 300) including the lens/sensor subassembly 318 is used with the treatment system 200. The optical path 350 may be aligned with a pupil of an eye of a patient such as the pupil 106 of FIG. 1A.

In some embodiments, the electrical element 328 is positioned off the optical path 350. Accordingly, the beam splitter 335 may be positioned, at least partially, on the optical path 350. The beam splitter 335 may be configured to direct a first portion 313 of the therapeutic radiation 316 towards the electrical element 328. The beam splitter 335 may be configured to transmit a second portion 315 of the therapeutic radiation 316 along the optical path 350. Some examples of the beam splitter 335 may include a partially transmitting mirror, a waveguide, or another suitable optical element. In some embodiments, multiple optical elements may be included in the lens/sensor subassembly 318 to direct a portion of the therapeutic radiation 316 towards the electrical element 328.

Accordingly, as the therapeutic radiation 316 is emitted towards an eye of a patient, the first portion 313 may be directed towards the electrical element 328, which may degrade the electrical element. The second portion 315 may be transmitted to the eye for treatment of an ocular disease. Following a particular amount of exposure to the second portion 315 of the therapeutic radiation 316, the electrical element 328 may no longer communicate the feedback data to the data transmission line 302. In some embodiments, the particular amount of exposure may be about 1000 emissions or shots of the therapeutic radiation.

In FIG. 4B, a direction 354 represents the direction in which the first portion 313 of the therapeutic radiation 316 is directed. The direction 354 is substantially perpendicular to the optical path 350. In other embodiments, the direction 354 may be at an angle of greater than 90 degrees or less than 90 degrees to the optical path 350.

In some embodiments, the data transmission line 302, the beam splitter 335, the electrical element 328, or some combination thereof are at least partially integrated into the contact lens 320. In these and other embodiments, integration may make the condition following degradation of the electrical element 328 (e.g., an electrical opening between the feedback sensor 324 and the data transmission line 302) permanent. For example, to repair degradation of the electrical element 328 integrated into the contact lens 320 may involve destruction of the contact lens 320. Accordingly, the degradation may prompt replacement of the lens/sensor subassembly 318 or of a contact lens assembly in which the lens/sensor subassembly 318 is incorporated.

In some embodiments, the electrical element 328 may be transparent or substantially transparent. In these and other embodiments, transparency of the electrical element 328 may increase difficulty associated with repair of the electrical element 328 following degradation.

Additionally or alternatively, in these and other embodiments, the electrical element 328 may be positioned at least partially along the optical path 350. For example, the electrical element 328 may extend from a first node 356 to the data transmission line 302 or across the volume defined by the ring-shaped PCB 333. In these embodiments, the beam splitter 335 may be omitted.

Figure 5A:
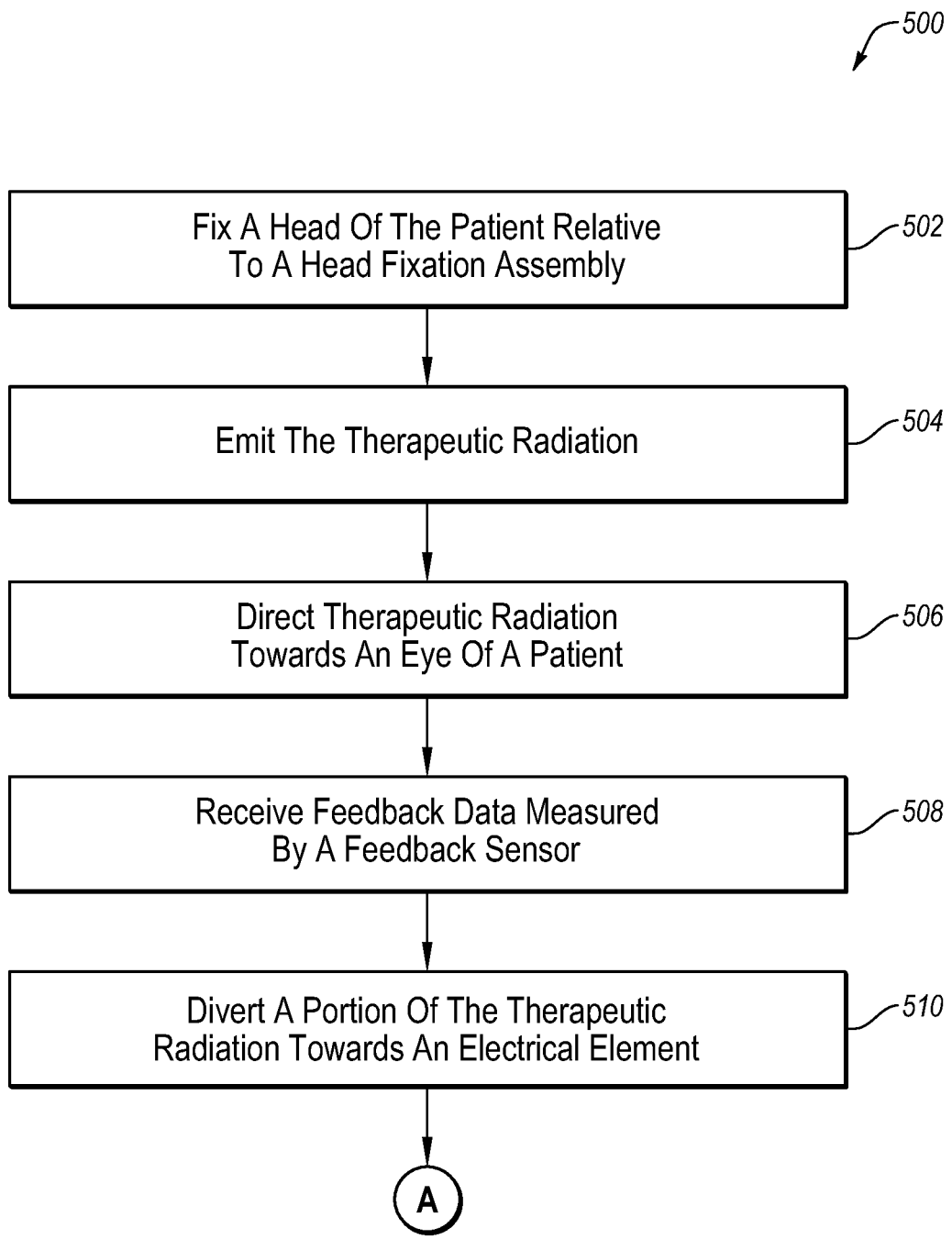
FIGS. 5A and 5B illustrate a flow diagram of an example method of laser-based ophthalmological treatment may be implemented in the system of FIGS. 2A-2C.
Figure 5B:
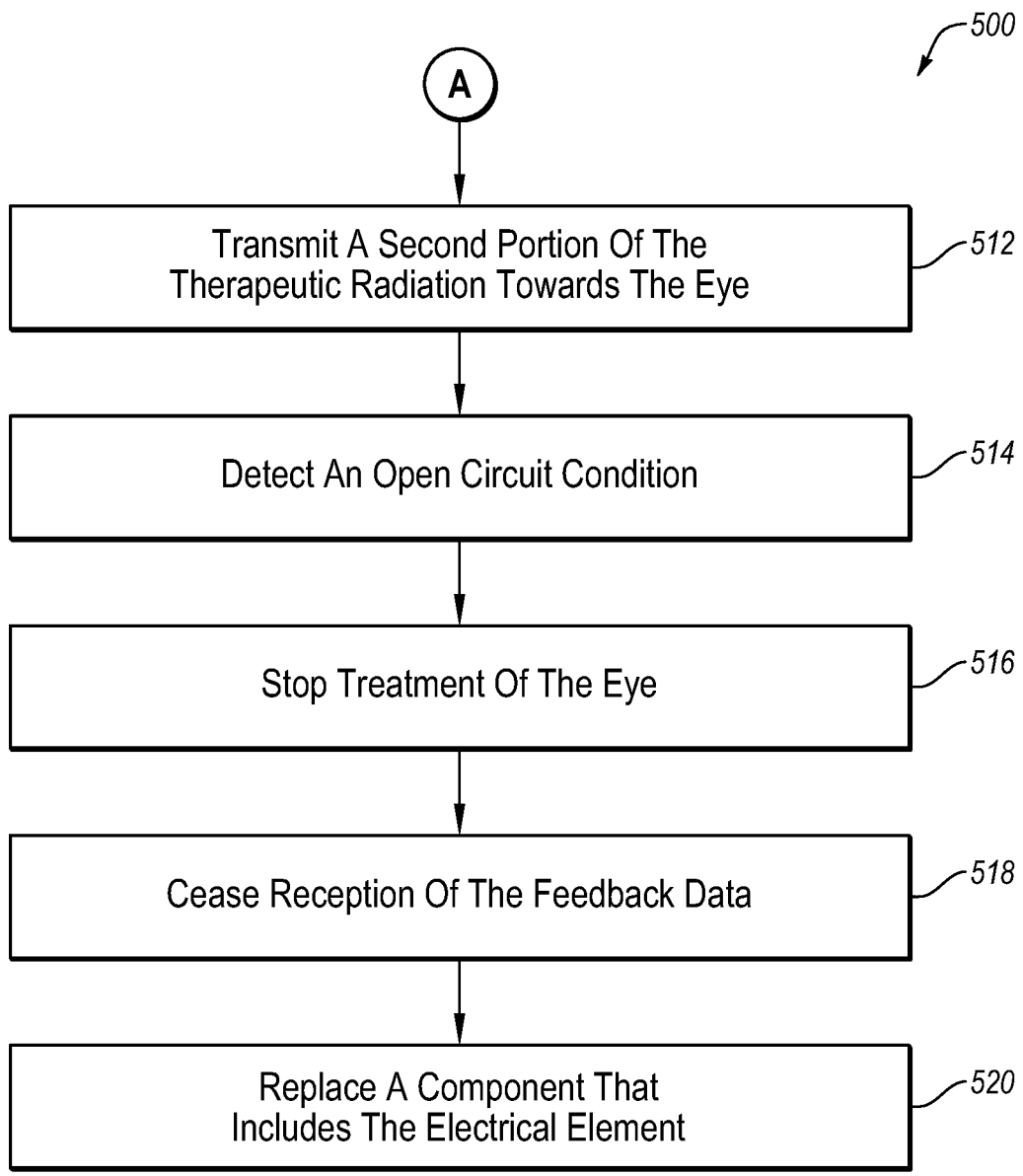

FIGS. 5A and 5B illustrate a flow diagram of an example method 500 of laser-based ophthalmological treatment, arranged in accordance with at least some embodiments described herein.

The method 500 may be performed, in whole or in part, in the treatment system 200, the contact lens assembly 300, the lens/sensor subassembly 400 and/or in other systems and configurations. Alternatively or additionally, the method 500 may be implemented at least partially by a processor device that performs or controls performance of one or more of the operations of the method 500. For instance, a computer (such as the computing device 700 of FIG. 7) or another processor device may be communicatively coupled to the treatment system 200, the contact lens assembly 300, or the lens/sensor subassembly 400 and may execute software or other computer-readable instructions accessible to the computer, e.g., stored on a non-transitory computer-readable medium accessible to the computer, to perform or control the treatment system 200, the contact lens assembly 300, or the lens/sensor subassembly 400 to perform the method 500 or a portion thereof.

The method 500 may include one or more of blocks 502, 504, 506, 508, 510, 512, 514, 516, 518, and 520. Although illustrated as discrete blocks, various blocks may be divided into additional blocks, supplemented with additional blocks, combined into fewer blocks, or eliminated, depending on the particular implementation. The method 500 may begin at block 502.

In block 502 ("Fix A Head Of The Patient Relative To A Head Fixation Assembly"), a head of a patient may be fixed relative to a head fixation assembly. The head fixation assembly may be configured to position and retain the head of the patient. For example, the head fixation assembly may be configured to position and retain the head of the patient relative to a therapeutic radiation treatment system. An example of the head fixation assembly may include the head fixation assembly 206 of FIGS. 2A-2C. Block 502 may be followed by block 504.

In block 504 ("Emit The Therapeutic Radiation"), therapeutic radiation may be emitted. The therapeutic radiation may include a pulsed-laser. For instance, in some embodiments, the therapeutic radiation may be emitted from a therapeutic radiation source such as the therapeutic radiation source 201 of FIG. 2C. Block 504 may be followed by block 506. In block 506 ("Direct Therapeutic Radiation Towards An Eye Of A Patient"), the therapeutic radiation may be directed towards an eye of the patient. For example, in some embodiments, the therapeutic radiation may be directed using a beam splitter or an optical waveguide. Block 506 may be followed by block 508.

In block 508 ("Receive Feedback Data Measured By A Feedback Sensor"), feedback data may be received. The feedback data may be measured by a feedback sensor. The feedback data may be indicative of a phenomenon in the eye during a therapeutic treatment. For example, the feedback data may be indicative of bubble formation as the therapeutic radiation is administered to an eye of the patient. The feedback data may be received prior to detection of the open circuit condition. Block 508 may be followed by block 510.

In block 510 ("Divert A Portion Of The Therapeutic Radiation Towards An Electrical Element"), a portion of the therapeutic radiation may be diverted towards an electrical element. Block 510 may be followed by block 512. In block 512 ("Transmit A Second Portion Of The Therapeutic Radiation Towards The Eye"), a second portion of the therapeutic radiation may be transmitted towards the eye. Block 512 may be followed by block 514. In block 514 ("Detect An Open Circuit Condition"), an open circuit condition may be detected. The open circuit condition may be detected of the electrical element after the electrical element is degraded by the portion of therapeutic radiation. Block 514 may be followed by block 516. In block 516 ("Stop Treatment Of The Eye"), treatment of the eye may stop. For example, the treatment of the eye may stop in response to detection of the open circuit condition. Block 516 may be followed by block 518. In block 518 ("Cease Reception Of The Feedback Data"), reception of the feedback data may cease. For example, the feedback data may no longer be received following detection of the open circuit condition. Block 518 may be followed by block 520. In block 520 ("Replace A Component That Includes The Electrical Element"), a component that includes the electrical element may be replaced. For instance, in some embodiments the component may include a contact lens, which may be replaced.

One skilled in the art will appreciate that, for this and other procedures and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the disclosed embodiments.

Figure 6A:
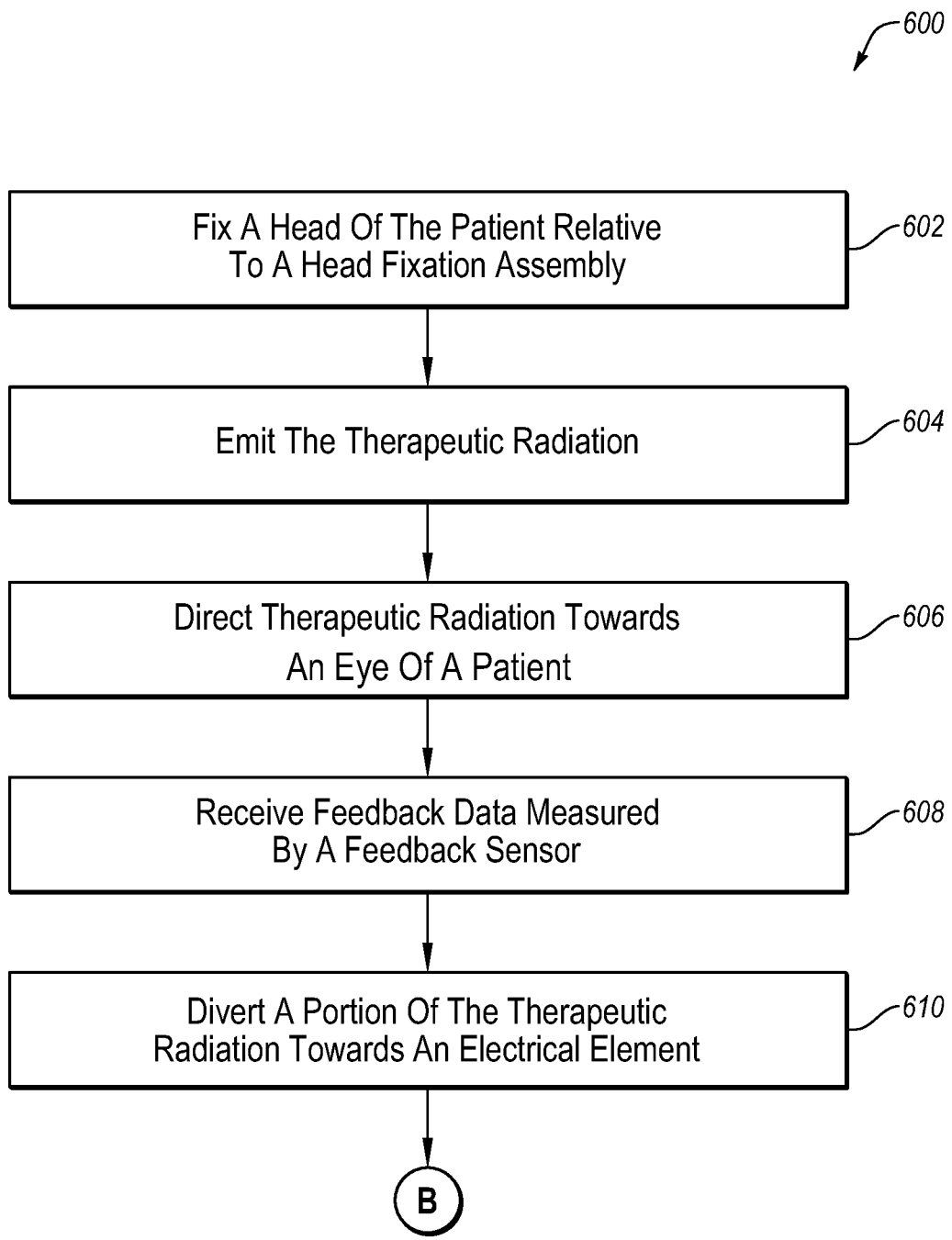
FIGS. 6A and 6B illustrate a flow diagram of an example method of preventing reuse of a contact lens assembly.
Figure 6B:
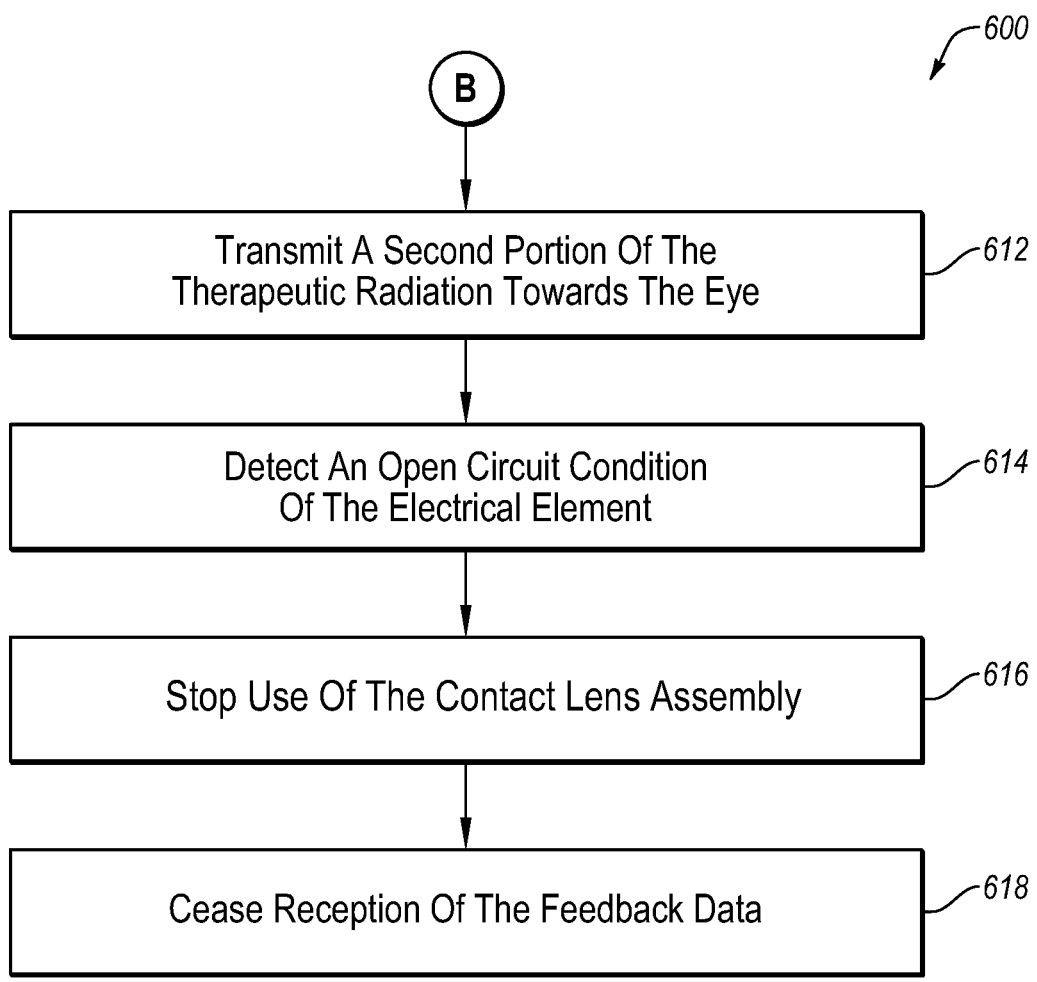

FIGS. 6A and 6B illustrate a flow diagram of an example method 600 preventing reuse of a contact lens assembly in a treatment system, arranged in accordance with at least some embodiments described herein.

The method 600 may be performed, in whole or in part, in the treatment system 200, the contact lens assembly 300, the lens/sensor subassembly 400 and/or in other systems and configurations. Alternatively or additionally, the method 600 may be implemented at least partially by a processor device that performs or controls performance of one or more of the operations of the method 600. For instance, a computer (such as the computing device 700 of FIG. 7) or another processor device may be communicatively coupled to the treatment system 200, the contact lens assembly 300, or the lens/sensor subassembly 400 and may execute software or other computer-readable instructions accessible to the computer, e.g., stored on a non-transitory computer-readable medium accessible to the computer, to perform or control the treatment system 200, the contact lens assembly 300, or the lens/sensor subassembly 400 to perform the method 600 or a portion thereof.

The method 600 may include one or more of blocks 602, 604, 606, 608, 610, 612, 614, 616, and 618. Although illustrated as discrete blocks, various blocks may be divided into additional blocks, supplemented with additional blocks, combined into fewer blocks, or eliminated, depending on the particular implementation. The method 600 may begin at block 602.

In block 602 ("Fix A Head Of The Patient Relative To A Head Fixation Assembly"), a head of a patient may be fixed relative to a head fixation assembly. The head fixation assembly may be configured to position and retain the head of the patient. For example, the head fixation assembly may be configured to position and retain the head of the patient relative to a therapeutic radiation treatment system. An example of the head fixation assembly may include the head fixation assembly 206 of FIGS. 2A-2C. Block 602 may be followed by block 604.

In block 604 ("Emit The Therapeutic Radiation"), therapeutic radiation may be emitted. The therapeutic radiation may include a pulsed-laser. For instance, in some embodiments, the therapeutic radiation may be emitted from a therapeutic radiation source such as the therapeutic radiation source 201 of FIG. 2C. Block 604 may be followed by block 606.

In block 606 ("Direct Therapeutic Radiation Towards An Eye Of A Patient"), the therapeutic radiation may be directed towards an eye of the patient through a contact lens assembly. For example, in some embodiments, the therapeutic radiation may be directed using a beam splitter or an optical waveguide. Block 606 may be followed by block 608.

In block 608 ("Receive Feedback Data Measured By A Feedback Sensor"), feedback data may be received. The feedback data may be measured by a feedback sensor. The feedback data may be indicative of a phenomenon in the eye during a therapeutic treatment. For example, the feedback data may be indicative of bubble formation as the therapeutic radiation is administered to an eye of the patient. The feedback data may be received prior to detection of the open circuit condition. Block 608 may be followed by block 610.

In block 610 ("Divert A Portion Of The Therapeutic Radiation Towards An Electrical Element"), a portion of the therapeutic radiation may be diverted towards an electrical element. Block 610 may be followed by block 612. In block 612 ("Transmit A Second Portion Of The Therapeutic Radiation Towards The Eye"), a second portion of the therapeutic radiation may be transmitted towards the eye. Block 612 may be followed by block 614. In block 614 ("Detect An Open Circuit Condition Of The Electrical Element"), an open circuit condition may be detected. The open circuit condition may be detected of the electrical element after the electrical element is degraded by the portion of therapeutic radiation. Block 614 may be followed by block 616. In block 616 ("Stop Use Of The Contact Lens Assembly"), treatment of the eye may stop. For example, the treatment of the eye may stop in response to detection of the open circuit condition. Block 616 may be followed by block 618. In block 618 ("Cease Reception Of The Feedback Data"), reception of the feedback data may cease. For example, the feedback data may no longer be received following detection of the open circuit condition.

Figure 7:
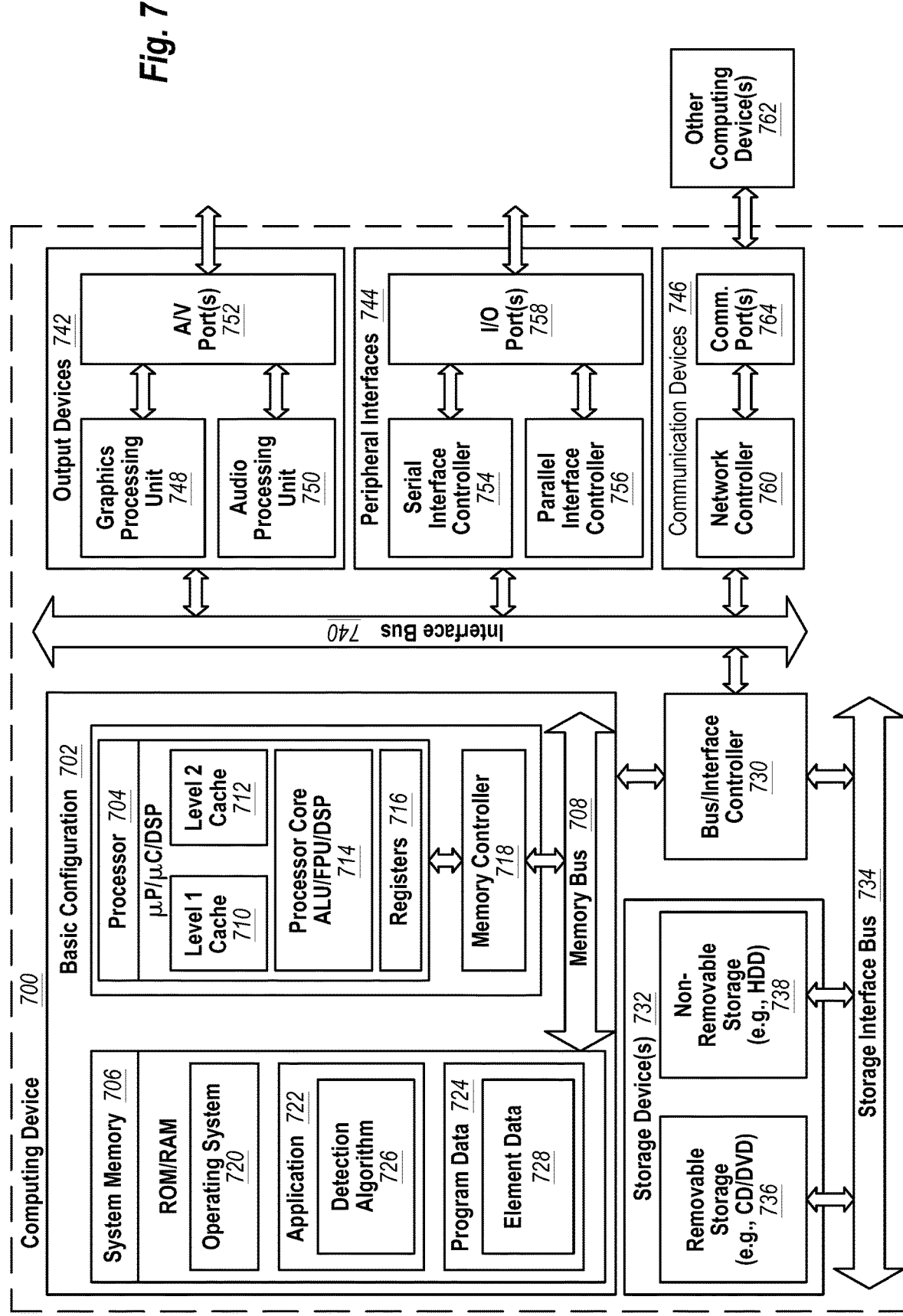
FIG. 7 illustrates a block diagram of an example computing device, all arranged in accordance with at least one embodiment of the present disclosure.

FIG. 7 illustrates a block diagram of an example computing device 700, in accordance with at least one embodiment of the present disclosure. The computing device 700 may be used in some embodiments to perform or control performance of one or more of the methods and/or operations described herein. For instance, the computing device 700 may be communicatively coupled to and/or included in the treatment system 200 of FIGS. 2A-2C to perform or control performance of the method 500 of FIGS. 5A and 5B or the method 600 of FIGS. 6A and 6B. In a basic configuration 702, the computing device 700 typically includes one or more processors 704 and a system memory 706. A memory bus 708 may be used for communicating between the processor 704 and the system memory 706.

Depending on the desired configuration, the processor 704 may be of any type including, such as a microprocessor (µP), a microcontroller (µC), a digital signal processor (DSP), or any combination thereof. The processor 704 may include one or more levels of caching, such as a level one cache 710 and a level two cache 712, a processor core 714, and registers 716. The processor core 714 may include an arithmetic logic unit (ALU), a floating point unit (FPU), a digital signal processing core (DSP Core), or any combination thereof. An example memory controller 718 may also be used with the processor 704, or in some implementations, the memory controller 718 may be an internal part of the processor 704. Depending on the desired configuration, the system memory 706 may be of any type, such as volatile memory (such as RAM), non-volatile memory (such as ROM, flash memory, or the like), or any combination thereof. The system memory 706 may include an operating system 720, one or more applications 722, and program data 724. The application 722 may include a degradation detection algorithm 726 that is arranged to detect degradation of an electrical element or another component that may prevent reuse or limit use of a contact lens assembly. The program data 724 may include element data 728. The element data 728 may include changes because of the degradation that may occur and resultant electrical resistance. Additionally, the program data 724 may include information used to alter or adjust the system based on the degradation of the electrical element. In some embodiments, the application 722 may be arranged to operate with the program data 724 on the operating system 720 to perform one or more of the methods and/or operations described herein, including those described with respect to FIGS. 5A-6B.

The computing device 700 may include additional features or functionality, and additional interfaces to facilitate communications between the basic configuration 702 and any other devices and interfaces. For example, a bus/ interface controller 730 may be used to facilitate communications between the basic configuration 702 and one or more data storage devices 732 via a storage interface bus 734. The data storage devices 732 may include removable storage devices 736, non-removable storage devices 738, or a combination thereof. Examples of removable storage and non-removable storage devices include magnetic disk devices such as flexible disk drives and hard-disk drives (HDDs), optical disk drives such as compact disk (CD) drives or digital versatile disk (DVD) drives, solid state drives (SSDs), and tape drives to name a few. Example computer storage media may include volatile and non-volatile, removable and non-removable media implemented in any method or technology for storage of information, such as computer-readable instructions, data structures, program modules, or other data.

The system memory 706, the removable storage devices 736, and the non-removable storage devices 738 are examples of computer storage media. Computer storage media includes, but is not limited to, RAM, ROM, EEPROM, flash memory or other memory technology, CD-ROM, digital versatile disks (DVDs) or other optical storage, magnetic cassettes, magnetic tape, magnetic disk storage or other magnetic storage devices, or any other medium which may be used to store the desired information and which may be accessed by the computing device 700. Any such computer storage media may be part of the computing device 700.

The computing device 700 may also include an interface bus 740 for facilitating communication from various interface devices (e.g., output devices 742, peripheral interfaces 744, and communication devices 746) to the basic configuration 702 via the bus/interface controller 730. The output devices 742 include a graphics processing unit 748 and an audio processing unit 750, which may be configured to communicate to various external devices such as a display or speakers via one or more A/V ports 752. The peripheral interfaces 744 include a serial interface controller 754 or a parallel interface controller 756, which may be configured to communicate with external devices such as input devices (e.g., keyboard, mouse, pen, voice input device, touch input device, and/or others), sensors, or other peripheral devices (e.g., printer, scanner, and/or others) via one or more I/O ports 758. The communication devices 746 include a network controller 760, which may be arranged to facilitate communications with one or more other computing devices 762 over a network communication link via one or more communication ports 764.

The network communication link may be one example of a communication media. Communication media may typically be embodied by computer-readable instructions, data structures, program modules, or other data in a modulated data signal, such as a carrier wave or other transport mechanism, and may include any information delivery media. A "modulated data signal" may be a signal that includes one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term "computer-readable media" as used herein may include both storage media and communication media.

The computing device 700 may be implemented as a portion of a small-form factor portable (or mobile) electronic device such as a cell phone, a personal data assistant (PDA), a personal media player device, a wireless web-watch device, a personal headset device, an application-specific device, or a hybrid device that includes any of the above functions. The computing device 700 may also be implemented as a personal computer including both laptop computer and non-laptop computer configurations.

The present disclosure is not to be limited in terms of the particular embodiments described herein, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of this disclosure. Also, the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that include A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that include A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

For any and all purposes, such as in terms of providing a written description, all ranges disclosed herein also encompass any and all possible sub ranges and combinations of sub ranges thereof. Any listed range can be easily recognized as sufficiently describing and enabling the same range being broken down into at least equal halves, thirds, quarters, fifths, tenths, and/or others. As a non-limiting example, each range discussed herein can be readily broken down into a lower third, middle third and upper third, etc. All language such as "up to," "at least," and the like include the number recited and refer to ranges which can be subsequently broken down into sub ranges as discussed above. Finally, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, various embodiments of the present disclosure have been described herein for purposes of illustration, and various modifications may be made without departing from the scope and spirit of the present disclosure. Accordingly, the various embodiments disclosed herein are not intended to be limiting.

What is claimed is:

1. A contact lens assembly comprising:
    an assembly housing that defines a first opening and a second opening that is opposite the first opening;
    an input lens positioned in the first opening;
    a lens/sensor subassembly positioned in the second opening, wherein the lens/sensor subassembly includes:
        a contact lens that is arranged in an optical path;
        a feedback sensor;
        a data transmission line configured to communicate feedback data measured by the feedback sensor to a laser-based ophthalmological treatment system;
        an electrical element that electrically couples the feedback sensor to the data transmission line; and
        a beam splitter that is partially positioned in the optical path,
    wherein:
        the beam splitter is configured to direct at least a portion of a therapeutic radiation towards the electrical element;
        the electrical element is configured to degrade responsive to exposure to the portion of the therapeutic radiation.

2. The contact lens assembly of claim 1, wherein the feedback sensor comprises at least one of an acoustic sensor, an ultrasonic sensor, or a ring shaped acoustic sensor positioned about at least a portion of the contact lens in the optical path.

3. The contact lens assembly of claim 1, wherein the electrical element comprises one or more of a wire mesh, an alloy metal that melts responsive to the at least a portion of the therapeutic radiation, or an electrical element that interrupts an electrical coupling between the feedback sensor and the data transmission line.

4. The contact lens assembly of claim 1, wherein the electrical element comprises one or more:
    an electrical element that is at least partially constructed of a conductive polymer;
    an electrical element that is at least substantially transparent;
    a wire mesh;
    an electrical element with an alloy metal that melts responsive to exposure to therapeutic radiation; or
    an electrical element that interrupts an electrical coupling between the feedback sensor and the data transmission line.

5. A lens/sensor subassembly comprising:
    a feedback sensor;
    a data transmission line configured to communicate feedback data measured by the feedback sensor to a laser-based ophthalmological treatment system; and
    an electrical element that is electrically coupled between the feedback sensor and the data transmission line, wherein the electrical element is configured to degrade in response to exposure to therapeutic radiation.

6. The lens/sensor subassembly of claim 5, further comprising a beam splitter that is configured to direct the therapeutic radiation towards the electrical element.

7. The lens/sensor subassembly of claim 6, further comprising a contact lens, wherein:
    the data transmission line, the beam splitter, and the electrical element are at least partially integrated into the contact lens; and
    the feedback sensor includes an electrical contact that is electrically coupled to the electrical element.

8. The lens/sensor subassembly of claim 5, wherein the feedback sensor includes an acoustic sensor.

9. The lens/sensor subassembly of claim 5, further comprising a contact lens, wherein the feedback sensor surrounds at least a portion of the contact lens such that feedback sensor is positioned outside of an optical path of the contact lens.

10. The lens/sensor subassembly of claim 9, further comprising a printed circuit board (PCB) that is electrically coupled to the feedback sensor and wherein the PCB substantially surrounds at least a portion of the contact lens.

11. The lens/sensor subassembly of claim 5, wherein the electrical element includes at least one of:
    an alloy metal that melts responsive to exposure to at least a portion of the therapeutic radiation;
    a conductive polymer;
    a transparent body; or
    a wire mesh.

12. A laser-based ophthalmological treatment system comprising:
    a therapeutic radiation source;
    a dosimetry board coupled to the therapeutic radiation source;
    the lens/sensor subassembly of claim 5 optically coupled to the therapeutic radiation source;
    a head fixation assembly configured to position and retain a head of a patient with an eye of a patient optically aligned to the lens/sensor subassembly to receive therapeutic radiation emitted by the therapeutic radiation source; and
    a microscope optically coupled to the lens/sensor subassembly.

13. The laser-based ophthalmological treatment system of claim 12, further comprising a patient contact lens assembly retainer configured to selectively retain the lens/sensor subassembly in the laser-based ophthalmological treatment system, wherein the lens/sensor subassembly is disposable and removable.

14. A method of laser-based ophthalmological treatment, the method comprising:
   directing therapeutic radiation towards an eye of a patient;
   diverting a portion of the therapeutic radiation towards an electrical element;
   detecting an open circuit condition of the electrical element after the electrical element is degraded by the portion of therapeutic radiation; and
   stopping treatment of the eye in response to detection of the open circuit condition.

15. The method of claim 14, further comprising:
   prior to detection of the open circuit condition, receiving feedback data measured by a feedback sensor, the feedback data being indicative of a phenomenon in the eye during a therapeutic treatment; and
   following detection of the open circuit condition, ceasing reception of the feedback data.

16. The method of claim 14, further comprising transmitting a second portion of the therapeutic radiation towards the eye.

17. The method of claim 14, further comprising replacing the electrical element.

18. The method of claim 14, further comprising emitting the therapeutic radiation as a pulsed-laser.

19. The method of claim 14, further comprising affixing a head of the patient relative to a head fixation assembly that is configured to position and retain the head of the patient.

20. The method of claim 14, further comprising preventing reuse of a contact lens assembly in a laser-based ophthalmological treatment system by:
   directing the therapeutic radiation towards an eye through a contact lens assembly;
   diverting the portion of the therapeutic radiation towards an electrical element associated with the contact lens assembly such that the electrical element degrades; and
   stopping use of the contact lens assembly when the open circuit condition is detected.

21. The method of claim 20, further comprising:
   prior to detection of the open circuit condition, receiving feedback data measured by a feedback sensor; and
   following detection of the open circuit condition, ceasing reception of the feedback data.

22. The method of claim 20, further comprising transmitting a second portion of the therapeutic radiation towards the eye.

* * * * *